US008871447B2

(12) United States Patent
Kayed et al.

(10) Patent No.: US 8,871,447 B2
(45) Date of Patent: Oct. 28, 2014

(54) IMMUNOGENS AND CORRESPONDING ANTIBODIES SPECIFIC FOR HIGH MOLECULAR WEIGHT AGGREGATION INTERMEDIATES COMMON TO AMYLOIDS FORMED FROM PROTEINS OF DIFFERING SEQUENCE

(75) Inventors: Rakez Kayed, Irvine, CA (US); Charles Glabe, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 1116 days.

(21) Appl. No.: 10/527,678

(22) PCT Filed: Sep. 12, 2003

(86) PCT No.: PCT/US03/28829
§ 371 (c)(1),
(2), (4) Date: May 9, 2006

(87) PCT Pub. No.: WO2004/024090
PCT Pub. Date: Mar. 25, 2004

(65) Prior Publication Data
US 2006/0280733 A1 Dec. 14, 2006

Related U.S. Application Data

(60) Provisional application No. 60/410,069, filed on Sep. 12, 2002.

(51) Int. Cl.
*G01N 33/53* (2006.01)
*A61K 39/00* (2006.01)
*C07K 16/18* (2006.01)
*C07K 16/00* (2006.01)

(52) U.S. Cl.
CPC ............. *A61K 39/0007* (2013.01); *C07K 16/18* (2013.01); *C07K 16/00* (2013.01)
USPC ........................................ 435/7.1; 424/184.1

(58) Field of Classification Search
None
See application file for complete search history.

(56) References Cited

U.S. PATENT DOCUMENTS

| 5,760,189 | A  | * | 6/1998  | Vicik et al. .................... 530/412 |
| 6,331,440 | B1 |   | 12/2001 | Nordstedt et al. |
| 6,703,015 | B1 | * | 3/2004  | Solomon et al. ............. 424/93.2 |
| 2001/0014455 | A1 | * | 8/2001 | Prusiner et al. ................ 435/7.1 |
| 2003/0185835 | A1 |   | 10/2003 | Braun |

FOREIGN PATENT DOCUMENTS

| EP | 0 613 007 | 2/1994 |
| WO | WO 89/06242 | 7/1989 |
| WO | WO 9707403 A1 * | 2/1997 |
| WO | WO 99/27944 | 6/1999 |
| WO | WO 02/03911 | 1/2002 |

OTHER PUBLICATIONS

Garzon-Rodriguez et al. JBC 275: 22645-22649, 2000.*
Wolf et al. The Embo Jour 9: 2079-2084, 1990.*
Ingenito et al. J. Am Chem Soc 121: 11369-11374, 1999.*
Tarrab et al. (J Gen Vir 76: 551-558, 1995).*
Hin et al (JBC 276: 48790-796, 2001).*
Harper et al. (Biochemistry 38: 8972-8980, 1999).*
Gorman et al. (Biopolymers (Pept Sci) 60: 381-394, 2001).*
Ladner RC (Trends in Biotech 13: 426-430, 1995).*
Glabe, C.G., *Conformation-dependent antibodies target diseases of protein misfolding*, TRENDS in Biochemical Sciences, Oct. 2004, vol. 29, No. 10, pp. 542-547.
Kirschner, D.A., *Synthetic peptide homologous to β protein from Alzheimer disease forms amyloid-like fibrils in vitro*, Proc. Natl. Acad. Sci. USA, Oct. 1987, vol. 84, pp. 6953-6957.
Kozin, S.A. et al., *Zinc Binding to Alzheimer's Aβ(1-16) Peptide Results in Stable Soluble Complex*, Biochemical and Biophysical Research Communications 2001, vol. 285, pp. 959-964.
McLaurin, J. et al., *Review: Modulating Factors in Amyloid-β Fibril Formation*, Journal of Structural Biology 2000, vol. 130, pp. 259-270.
Tjernberg, L.O. et al., *Assembling amyloid fibrils from designed structures containing a significant amyloid β-peptide fragment*, Biochem. J. 2002, vol. 366, pp. 343-351.
Supplementary European Search Report (EP 03752350.3), mailed Jun. 20, 2007.
Atwood C.S., et al., "Dramatic Aggregation of Alzheimer Abeta by Cu(II) is induced by conditions representing physiological acidosis", The Journal of Biological Chemistry, vol. 272, No. 21, 12817-12826, 1998.
Kawahara, M. et al, "Aluminium promotes the aggregation of Alzheimer's amyloid beta-protein in vitro", Biochemical and Biophysical Research Communications, vol. 198, No. 2, 1994, 531-535.
T. Miura et al, "Metal binding modes of Alzheimer's amyloid beta-peptide in insoluble aggregates and soluble complexes", Biochemistry, 2000, 39,7024-7031.
S. Chen at al, Amyloid-like Features of Polyglutamine Aggregates and Their Assembly Kinetics, Biochemistry, 2002, vol. 41, pp. 7391-7399.

* cited by examiner

*Primary Examiner* — Daniel E Kolker
*Assistant Examiner* — Aditi Dutt
(74) *Attorney, Agent, or Firm* — Robert D. Buyan; Stout, Uxa & Buyan, LLP

(57) ABSTRACT

Compositions of matter that comprise one or more conformational epitopes found on amyloid peptide aggregates, antibodies to such epitopes and methods for making and using the compositions, eptitopes and/or antibodies. The invention includes synthetic or isolated compositions that contain or consist of certain conformational epitopes that are found on peptide aggregates (e.g., toxic peptide aggregates) present in human or veterinary patients who suffer from, or who are likely to develop, amyloid diseases (e.g., Alzheimer's Disease). The invention includes methods for the detection, treatment and prevention of diseases in humans or animals, using such compositions. The invention further includes antibodies which bind to the conformational epitopes as well as methods for making such antibodies and methods for the detection, treatment and prevention of diseases and/or identification of potential therapies (e.g., drug screening) using such antibodies.

19 Claims, 11 Drawing Sheets

Soluble low MW Aß40 (▲)
Aß40 fibrils (■)
Soluble Aß40 oligomers (O)

| Time (hrs) | | 6 | 24 | 48 | 168 | 336 | 504 |
|---|---|---|---|---|---|---|---|
| anti-Oligo. | Aβ42 | ● | ● | ● | ● | | |
| | Aβ40 | | ● | ● | ● | ● | |

| Time (hrs) | | 6 | 24 | 48 | 168 | 336 | 504 |
|---|---|---|---|---|---|---|---|
| 6E10 | Aβ42 | ● | ● | ● | ● | ● | ● |
| | Aβ40 | ● | ● | ● | ● | ● | ● |

Figure 4

( — · — ) Aβ40 incubated in 50 mM Tris (pH 7.4) 100mM NaCl for 2 days ( — — — ) Aβ40 Freshly dissolved in 50 mM Tris (pH 7.4), ( ......... ) Aβ40 incubated in 50 mM Tris (pH 7.4) for 2 days.

Inhibition of Aβ40 and Aβ42 soluble oligomer toxicity by anti-oligomer. Samples were preincubated with (open bars) without (filled bars) an excess of affinity purified anti-oligomer antibody for 30 min or with an equivalent amount of non-immune rabbit IgG (hatched bars) and then assayed for cytotoxicity at a final concentration of 2.5 μM using MTT.

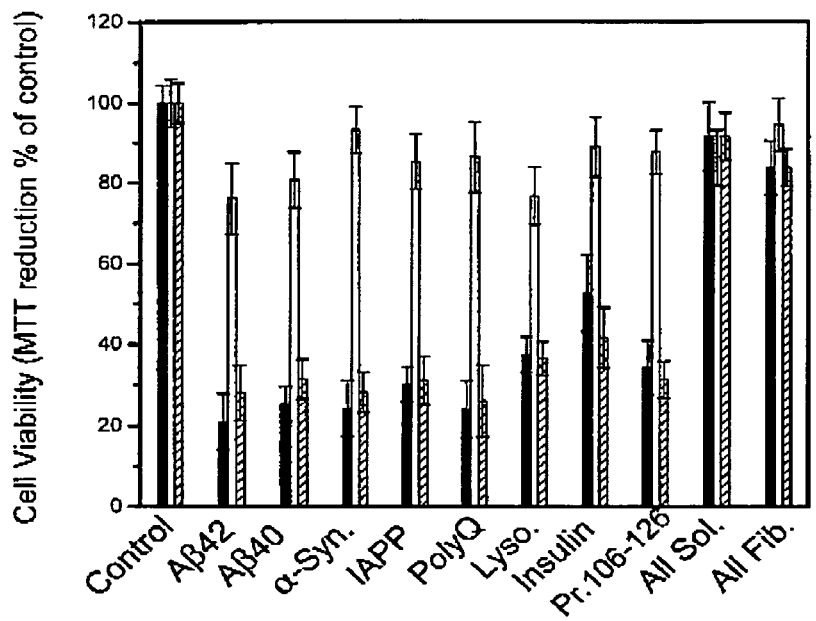

Inhibition of the toxicity of other types of soluble oligomers by anti-oligomer antibody. The soluble oligomer samples were preincubated with (open bars) or without (filled bars) an excess of affinity purified anti-oligomer antibody or with an equivalent amount of non-immune rabbit IgG (hatched bars) for 30 min and then assayed for cytotoxicity at a final concentration of 2.5 µM using the MTT reduction assay.

Figure 8

Filled bars: Soluble oligomers without antibody

Open bars: Soluble oligomers incubated with anti-oligomer IgG

Hatched bars: Soluble oligomers incubated with control, non-immune IgG.

Solid bars: Soluble oligomers in the absence of Fabs

Open bars: Soluble oligomers incubated with anti-oligomer Fabs

IMMUNOGENS AND CORRESPONDING ANTIBODIES SPECIFIC FOR HIGH MOLECULAR WEIGHT AGGREGATION INTERMEDIATES COMMON TO AMYLOIDS FORMED FROM PROTEINS OF DIFFERING SEQUENCE

FIELD OF THE INVENTION

The invention relates generally to the fields of medicine, immunology and protein biochemistry and more particularly to certain antigenic compositions and antibodies that are useful in the diagnosis, treatment and/or modeling of amyloid diseases.

BACKGROUND OF THE INVENTION

Many biological functions come about, at least in part, due to the ability of proteins to adopt various sequence-dependent structures. However, certain protein sequences can sometimes form aberrant, misfolded, insoluble aggregates known as amyloid fibrils. These amyloid fibrils are thought to be involved in the pathogenesis of various amyloid diseases of genetic, infectious and/or spontaneous origin, including spongiform encephalopathies, Alzheimer's disease, Parkinson's disease, type II diabetes, Creutzfeldt-Jakob disease, Huntington's disease, possibly macular degeneration, various prion diseases and numerous others. In at least some of these amyloid diseases, amyloid fibrils lead to the development of amyloid plaques.

Amyloid peptides are the principal constituent of amyloid plaques. In the case of Alzheimer's disease, the peptides are termed Aβ or β-amyloid peptide. Aβ peptide is an internal fragment of 39 to 43 amino acids of amyloid precursor protein (APP). Several mutations within the APP protein have been correlated with the presence of AD. See, for example, Goate et al., Nature, (1991) 349, 704 (valine to isoleucine); Chartier Harlan et al., Nature (1991) 353,844 (valine to glycine); Murrell et al. Science (1991) 254,97 (valine to phenylalanine); Mullan et al., Nature Genet. (1992) 1,345 (a double mutation changing lysine 595-methionine596 to asparagine595-leucine596). Such mutations are thought to cause AD by producing an increased or altered processing of APP to A. In particular, the processing of APP resulting in accumulation of the longer forms of A, for example, A1-42 and A1-43 is thought to be important in the cause of AD. Mutations in other genes, such as the presenilin genes PS1 and PS2, are thought to indirectly affect processing of APP resulting In production of the long form of A. See, for example, Hardy, TINS (1997) 20,154.

European Patent Publication EP 526,511 (McMichael) and PCT International Patent Publication WO/9927944 (Schenk) have described the administration of Aβ to patients for the treatment or prevention of Alzheimer's. However, although active immunization of Aβ to transgenic mice produces apparent benefits, the extension of this approach to AD patients has resulted in undesirable inflammation of the central nervous system in some of the subjects. See Hardy, D. J. Selkoe (2002) Science 297, 353-356.

Soluble Aβ includes Aβ monomers as well as aggregations of such monomers referred to as protofibrillar aggregates. These protofibrillar aggregates lead to the development of amyloid fibrils. Soluble Aβ content of the human brain is better correlated with the severity of AD than is the accumulation of amyloid plaques. See, for example, Y. M. Kuo et al. (1996) J. Biol. Chem. 271, 4077-4081; C. A. McLean et al. (1999) Annals of Neurology 46, 860-6; L. F. Lue et al. (1999) American Journal of Pathology 155, 853-862. In addition, recent reports suggest that the toxicity of Aβ and other amyloidogenic proteins lies not in the soluble monomers or insoluble fibrils that accumulate, but rather in the protofibrillar aggregates. See, for example, Hartley et al. (1999), Journal of Neuroscience 19, 8876-8884; Lambert et al., Proceedings of the National Academy of Sciences of the United States of America (1998) 95, 6448-53; and Bucciantini et al., Nature (2002) 416, 507-511; and Hartley et al. Nature (2002) 418, 291. Taken together, these results indicate that the protofibrillar aggregates may be more pathologically significant than other forms of the amyloid peptides and therefore may be a more desirable target in the prevention or curing of amyloid diseases such as AD.

There is a need for the development of an antigens capable of producing antibodies which bind to the toxic form of amyloid with high specificity, thereby inhibiting the pathogenesis of amyloid diseases.

SUMMARY OF THE INVENTION

The present invention provides antigens useful for producing antibodies which specifically bind Aβ peptide aggregates and do not bind soluble, low molecular weight Aβ or Aβ fibrils. Also, these antibodies specifically recognize amyloid peptide aggregates produced from all other types of amyloidogenic peptides and proteins examined herein while not binding to the corresponding low molecular weight amyloid peptides or fibrils.

In accordance with the present invention, there are provided isolated compositions, for example, antigenic compositions, which include an epitope, for example, a conformational epitope, of a protofibrillar aggregate that forms in a human or animal and contributes to amyloid fibril formation. Amyloid fibrils may be free of the epitopes or substantially free of the epitopes of the compositions. In addition, amyloid peptide monomers may be free of the epitopes or substantially free of the epitopes of the compositions. Also provided for are compositions which include antibodies which bind to these epitopes. In one embodiment, the compositions are isolated from a natural source. In another embodiment, the compositions are synthetic. In one useful embodiment, the compositions are pharmaceutical compositions, for example vaccines. Still further in accordance with the invention, the compositions include a peptide or a protein that may be conformationally constrained. The peptides may be isolated form nature or may be synthetic. In one embodiment, the peptide is selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9 and mixtures thereof.

Still further in accordance with the present invention, the compositions are supported by a surface which may be of any shape including curved or flat. In one useful embodiment, the surface comprises solid matter. The surface may be a film, a particle or a sheet. In one embodiment, the surface is functionally modified, for example, functionally modified allowing for the formation of self assembled peptide monolayers. In addition, the surface may comprise a protein, for example, a -pleated sheet. In one embodiment, peptides are bound to the support surface. For example, the peptides may be chemically bonded to the support surface. Chemical bonds include ionic bonds, hydrogen bonds, covalent bonds and van der Waals attraction. In one particularly useful embodiment, the chemical bond is a covalent bond. The compositions may comprise a linker effective to attach the peptides to the surface. The linkers may include, without limitation, streptavidin, hydrocarbon molecules, such as hydrocarbon chains, including, but not limited to, citrate, HS—$(CH_2)_n$—COOH, HS—$(CH_2)_n$—$NH_2$, HS—$(CH_2)_n$—OH, HS—$(CH_2)_n$—COOR, phosphoramide —$NH_2$, cyclic or acidic disulfide-R—COOH, cyclic or acidic disulfide-R—$NH_2$, Si$(OCH_3)$3-R—$NH_2$, Si$(OCH_3)$3-R—COOH and -maleimide. The support may comprise any suitable material including, but not limited to, gold, zinc, cadmium, tin, titanium, silver, selenium, gallium, indium, arsenic, silicon, mixtures thereof or combinations thereof.

Sill further in accordance with the present invention, protofibrillar aggregates as described herein may have a molecular weight in a range of about 10 kDa to about 100,000,000 kDa. In one embodiment, the protofibrillar aggregate comprises five monomers. In another embodiment, the protofibrillar aggregate comprises eight monomers. The protofibrillar aggregate is present in a human or animal having a disease characterized by amyloid deposits and may comprise a toxic species. The invention provides for antibodies which may be effective to reduce the toxicity of protofibrillar aggregates.

Still further in accordance with the present invention, the protofibrillar aggregate is present in a human or animal having a disease characterized by amyloid deposits. For example, the disease may be Alzheimer's, early onset Alzheimer's associated with Down's syndrome, SAA amyloidosis, hereditary Icelandic syndrome, multiple myeloma, and spongiform encephalopathies (such as bovine spongiform encephalopathy (BSE), mad cow disease, sheep scrapie, and mink spongiform encephalopathy), Parkinson's disease, Huntington's disease, amyotropic lateral sclerosis, Creutzfeld Jakob disease, Gerstmann-Straussler-Scheinker syndrome, kuru, fatal familial insomnia, chronic wasting syndrome, familial amyloid polyneuropathy, frontotemporal dementia, type II diabetes, systemic amyloidosis, serum amyloidosis, British familial dementia, Danish familial dementia, macular degeneration, cerebrovascular amyloidosis, a prion disease or another amyloid disease.

Still further in accordance with the present invention, there are provided methods of preventing or treating a disease or condition in a human or animal subject, the disease or condition being characterized by the presence of amyloid deposits. The methods may include administering to the subject a therapeutically effective or preventative amount of a composition. In one embodiment, the method includes inducing an immune response against the conformational epitope.

Still further in accordance with the present invention, there are provided methods of preventing or treating a disease or condition characterized by amyloid deposits in a human or animal which include causing an antibody to bind to a conformational epitope of a protofibrillar aggregate that forms in a human or animal and contributes to fibril formation. In one embodiment, the methods include administering an antibody. The composition may be administered by intraspinal, intrathecal, oral, transdermal, pulmonary, intravenous, subcutaneous, intramuscular, intranasal, rectal, sublingual or buccal administration.

Still further in accordance with the present invention, there are provided methods of making an antibody which may include administering to a human or animal a composition of the invention. The method may also include recovering the antibody from the human or animal.

Still further in accordance with the present invention, there are provided methods of diagnosing a disease characterized by amyloid deposits which include combining tissue or fluid from a human or animal patient and an antigenic composition of the invention or an antibody of the invention. In one embodiment, the tissue or fluid is cerebrospinal fluid. The disease includes, without limitation, Alzheimer's, early onset Alzheimer's associated with Down's syndrome, SAA amyloidosis, hereditary Icelandic syndrome, multiple myeloma, and spongiform encephalopathies, including mad cow disease, sheep scrapie, and mink spongiform encephalopathy, Parkinson's disease, Huntington's disease, amyotropic lateral sclerosis, Creutzfeld Jakob disease, Gerstmann-Straussler-Scheinker syndrome, kuru, fatal familial insomnia, chronic wasting syndrome, transthyretin-related amyloidosis, for example, familial amyloid polyneuropathy and serum amyloidosis, frontotemporal dementia, type II diabetes, systemic amyloidosis, British familial dementia, Danish familial dementia, macular degeneration and cerebrovascular amyloidosis. The amounts of antibody may be measured as antibody titers. In one embodiment, amounts of antibody are measured using an ELISA assay.

Still further in accordance with the present invention, there are provided methods of assessing efficacy of a treatment method of a human or animal having a disease characterized by amyloid deposits which may include determining a baseline amount of an antibody specific for an antigen comprising a composition of the invention in tissue sample from a patient before treatment with an agent and comparing an amount of the antibody in the tissue sample from the subject after treatment with the agent to the baseline amount of the antibody. In one embodiment, a reduction or lack of significant difference between the amount of the antibody measured after the treatment compared to the baseline amount of the antibody indicates a negative treatment outcome. In another embodiment, a significantly greater amount of the antibody measured after the treatment compared to the baseline amount of the antibody indicates a positive treatment outcome.

Still further in accordance with the present invention, there are provided methods of assessing efficacy of a treatment method of a human or animal having a disease characterized by amyloid deposits which may include determining a baseline amount of a protofibrillar aggregate specific for an antibody of the invention in tissue sample from a patient before treatment with an agent and comparing an amount of the protofibrillar aggregate specific for an antibody of the invention in the tissue sample from the subject after treatment with the agent to the baseline amount of the protofibrillar aggregate. In one embodiment, a reduction or lack of significant difference between the amount of the protofibrillar aggregate measured after the treatment compared to the baseline amount of the protofibrillar aggregate indicates a negative treatment outcome. In another embodiment, a significantly greater amount of the protofibrillar aggregate measured after the treatment compared to the baseline amount of the protofibrillar aggregate indicates a positive treatment outcome.

Still further in accordance with the present invention, there are provided methods of monitoring amyloid disease or susceptibility thereto in a human or animal that may include detecting an immune response against a composition of the invention in a sample from the patient.

Still further in accordance with the present invention, the amounts of antibody may be measured as antibody titers and the amounts of antigen may be measured as antigen titers. In one embodiment, the amounts of antibody are measured by an ELISA assay. In one embodiment, the amounts of antigen are measured by an ELISA assay.

Sill further in accordance with the present invention, the detecting of an immune response may include detecting an antibody that specifically binds to a composition of the invention and/or detecting T-cells specifically reactive with a composition of the invention.

Still further in accordance with the present invention, there are provided diagnostic kits useful for detecting a disease characterized by amyloid deposits which may include an isolated composition of the invention which includes an antigen of the Invention or an antibody of the invention.

Each and every feature described herein, and each and every combination of two or more of such features, is included within the scope of the present invention provided that the features included in such a combination are not mutually inconsistent.

These and other aspects and advantages of the present invention are set forth in the following figures, detailed description, examples and claims.

BRIEF DESCRIPTION OF THE FIGURES

FIG. 4 shows the results of a dot blot assay demonstrating the formation of Aβ high molecular weight oligomers from Aβ low molecular weight oligomers and, in turn, the formation of Aβ fibrils from Aβ high molecular weight oligomers, each over time.

FIG. 8 shows the reduction in cell toxicity of low molecular weight aggregates (Sol.), high molecular weight aggregates and fibrils (Fib.) of A 40, A42, synuclein, islet amyloid polypeptide (IAPP), poly glutamine, lysozyme, human insulin and human prion peptide 106-126 by anti-oligomer antibody using the MTT reduction assay.

DEFINITIONS

Figure 1:
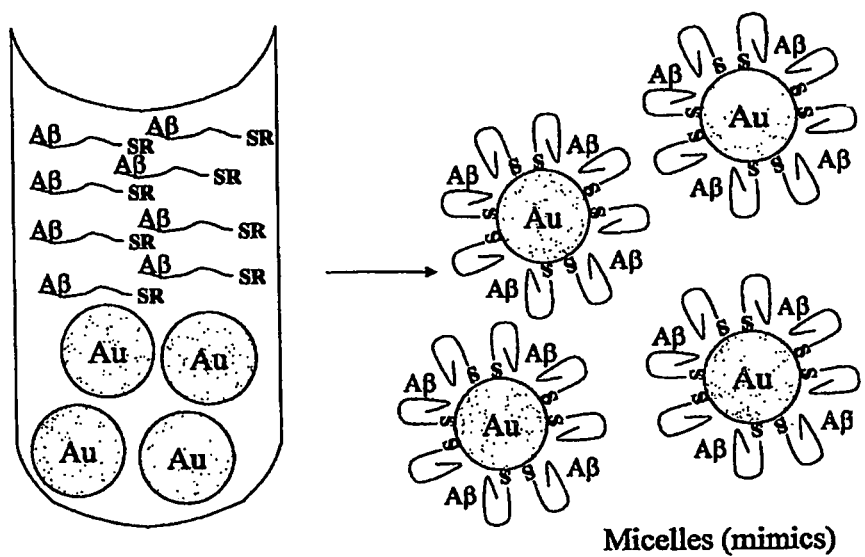
FIG. 1 shows the assembly of a synthetic antigen of the invention.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "A" or "Aβ peptide" refers to peptides which comprise low molecular weight soluble oligomers, protofibrillar aggregates, fibrils and amyloid deposits each associated with AD. Amyloid Aβ peptides include, without limitation, Aβ 39, Aβ 40, Aβ 41 Aβ 42 and Aβ 43 which are 39, 40, 41, 42 and 43 amino acid amino acids in length, respectively.

An "amyloid peptide" is a peptide that is present in amyloid forms including amyloid peptide intermediates, low molecular weight soluble oligomers, amyloid fibrils and amyloid plaques.

The term "antibody" is used to include intact antibodies and binding fragments thereof, including but not limited to, for example, full-length antibodies (e.g., an IgG antibody) or only an antigen binding portion (e.g., a Fab, $F(ab')_2$ or scFv fragment). Typically, fragments compete with the intact antibody from which they were derived for specific binding to an antigen. Optionally, antibodies or binding fragments thereof, can be chemically conjugated to, or expressed as, fusion proteins with other proteins.

"Anti-oligomer antibody" or "Anti-oligomer" refer to an antibody that binds to amyloid peptide aggregate intermediates but does not bind to or does not specifically bind to amyloid peptide monomers, dimers, trimers or tetramers.

Compositions or methods "comprising" one or more recited elements may include other elements not specifically recited. For example, a composition that comprises an amyloid Aβ peptide may encompass both an isolated amyloid Aβ peptide as a component of a larger polypeptide sequence or as part of a composition which includes multiple elements.

The term "epitope" or "antigenic determinant" refers to a site on an antigen to which B and/or T cells respond or a site on a molecule against which an antibody will be produced and/or to which an antibody will bind. For example, an epitope can be recognized by an antibody defining the epitope.

A "linear epitope" is an epitope wherein an amino acid primary sequence comprises the epitope recognized. A linear epitope typically includes at least 3, and more usually, at least 5, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the antibody defining the epitope). Typically a conformational epitope comprises an increased number of amino acids relative to a linear epitope. With regard to recognition of conformational epitopes, the antibody recognizes a 3-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography 2-dimensional nuclear magnetic resonance spectroscopy and site-directed spin labeling and electron paramagnetic resonance spectroscopy. See, for example, Epitope Mapping Protocols in Methods in Molecular Biology, Vol. 66, Glenn E. Morris, Ed. (1996), the disclosure of which is incorporated in its entirety herein by reference.

The term "immunological response" or "immune response" relates to the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity.

An "immunogenic agent" or "immunogen" or "antigen" is capable of inducing an immunological response against itself upon administration to a subject, optionally in conjunction with an adjuvant.

"Isolated" means purified, substantially purified or partially purified. Isolated can also mean present in an environment other than a naturally occurring environment. For example, an antibody that is not present in the whole blood serum in which the antibody would ordinarily be found when naturally occurring is an isolated antibody.

"Low molecular weight aggregate", "low molecular weight amyloid aggregate", "low molecular weight oligomer" and "low molecular weight soluble oligomer" refer to amyloid peptides present in aggregates of less than four or five peptides. In one specific example, low molecular weight Aβ refers to the low molecular weight soluble oligomers found associated with AD.

The term "patient" includes human and other animal subjects that receive therapeutic, preventative or diagnostic treatment or a human or animal having a disease or being predisposed to a disease.

"Protofibrillar aggregates", "micellar aggregates", "high molecular weight aggregation intermediates," "high molecular weight amyloid peptide aggregates", "high molecular weight soluble amyloid peptide aggregates" "amyloid peptide aggregates", "soluble aggregate intermediates", "amyloid oligomeric intermediates", "oligomeric intermediates" and "oligomeric aggregates" or simply, "intermediates" refer to aggregations which include more than three individual peptide or protein monomers, for example, more than four peptide or protein monomers. The upper size of protofibrillar aggregates includes aggregations of oligomers which form spherical structures or micelles and stings of micelles which lead to fibril formation.

"Annular protofibrils" are a particular subset of protofibrillar aggregates in which 3 to 10 spherical oligomer subunits are arranged in an annular or circular fashion with a hollow center that appears as a pore in electron or atomic force micrographs.

The molecular weight of a protofibrillar aggregate may be in a range of about 10 kDa to about 100,000,000 KDa, for example, about 10 kDa to about 10,000,000 or 1,000,000 KDa. However, this size range is not intended to be limiting and protofibrillar aggregates are not defined by a molecular weight range.

"Protofibrils" are protofibrillar aggregates which include spherical structures comprising amyloid Aβ peptides that appear to represent strings of the spherical structures forming curvilinear structures.

"Specific binding" between two entities means an affinity of at least $10^6$, $10^7$, $10^8$ $10^9$ M$^{-1}$, or $10^{10}$ M$^{-1}$. Affinities greater than $10^8$ M$^{-1}$ are preferred for specific binding.

The term "substantial identity" means that two peptide sequences, when optimally aligned, such as by the programs GAP or BESTFIT using default gap weights, share at least 65 percent sequence identity, for example, at least 80 percent or 90 percent sequence identity, or at least 95 percent sequence identity or more, for example, 99 percent sequence identity or higher.

Preferably, residue positions in an alignment which are not identical differ by conservative amino acid substitutions, i.e., substitution of an amino acid for another amino acid of the same class or group. Some amino acids may be grouped as follows: Group I (hydrophobic side chains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Non-conservative substitutions may include exchanging a member of one of these classes for a member of another class.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm may then be used to calculate the percent sequence identity for the test sequence (s) relative to the reference sequence, based on the designated program parameters. Optimal alignment of sequences for comparison can be conducted, for example, by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information. Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix, see for example, Henikoff & Henikoff, Proc. Natl. Acad. Sci. USA 89,10915 (1989). Conservative substitutions involve substitutions between amino acids in the same class.

"Synthetic" mean not naturally occurring. For example, a synthetic composition is a composition that is not found occurring in nature in whole or in part.

A "therapeutic agent" or "therapeutic" is a substance useful for the treatment or prevention of a disease in a patient. Therapeutic agents of the invention are typically substantially pure. This means that an agent is typically at least about 50% w/w (weight/weight) pure, as well as being substantially free from proteins and contaminants which interfere with the efficacy of the therapeutic. The agents may be at least about 80% w/w and, more preferably at least 90% w/w or about 95% w/w in purity. However, using conventional protein purification techniques, homogeneous peptides of 99% w/w or more can be produced.

DETAILED DESCRIPTION OF THE INVENTION

The present invention provides for compositions having one or more epitopes found on amyloid peptide aggregates which are present in humans or animals having a disease characterized by amyloid deposits, antibodies to such epitopes and methods for making and using the compositions and antibodies.

More particularly, the invention includes, without limitation, compositions comprising an epitope, for example, a conformational epitope, found on a peptide aggregate, for example, an amyloid peptide aggregate in a human or animal having a disease characterized by amyloid deposits, methods of making the compositions, methods of using the compositions including, without limitation, for the detection, treatment and prevention of diseases, antibodies against the conformational epitopes present on the compositions, methods of making the antibodies and methods of using the antibodies including, without limitation, for the detection, treatment and prevention of diseases.

Amyloid diseases are characterized by the accumulation of amyloid plaques or precursors to amyloid plaques in patients or the predisposition to the accumulation of amyloid plaques or precursors to amyloid plaques in patients. One of the primary constituents of amyloid plaques are amyloid peptides. The general conformation of amyloid peptides may vary from disease to disease, but often the peptide has a characteristic-pleated sheet structure. Amyloid peptides include peptides and proteins of about 10 or about 20 amino acids to about 200 amino acids in length. Though this size range is not intended as a limitation and amyloid peptides or proteins having fewer or more amino acids are contemplated in the present invention.

Protofibrillar aggregates are intermediates in the production of insoluble fibrils that accumulate in amyloid plaques of humans or animals having a disease characterized by amyloid deposits, for example, Alzheimer's disease. Protofibrillar aggregates include aggregates which may be as small as four amyloid peptides, as small as five amyloid peptides, as small as six amyloid peptides, as small as seven amyloid peptides or as small as eight amyloid peptides. In one embodiment, protofibrillar aggregates are micellar aggregates or micelles or strings of micelles. Protofibrillar aggregates are effective to form a conformational epitope which is recognized by an antibody of the present invention.

The conformational epitopes of the present invention which are found on protofibrillar aggregates are substantially not found in the native precursor proteins for amyloid peptides, for example, amyloid peptide monomers, dimers, trimers or tetramers nor in the mature amyloid fibers that are defined by their characteristic cross β x-ray fiber diffraction pattern or in amyloid plaques. The protofibrillar aggregates that contain the specific polypeptide structure which results in conformational epitopes that are recognized by antibodies of the present invention have a size range of approximately a pentamer, a hexamer, a heptamer or an octamer to micellar forms or protofibrils which have a molecular weight in excess of 1,000,000 Daltons. Immunogens of the present invention include compositions comprising these epitopes. Antibodies of the invention are effective to bind to these epitopes.

Immunogens of the present invention may be obtained from any suitable source. For example, the immunogens may be purified from naturally occurring sources. In one particularly useful embodiment, the immunogens are synthetic.

Immunogens displaying the epitope necessary to produce antibodies of the present invention may be prepared as oligomeric intermediate mimics comprising amyloid peptides or proteins. For example, A peptides, such as A 40 and A 41, synuclein, IAPP(C2A and C7A) where alanine is substituted for the naturally occurring cysteine in IAPP, Polyglutamine KKQ40KK (SEQ ID NO: 5) or poly glutamine where the number of Q residues is greater than 32, Calcitonin, TTR and its mutants TTR Pro$^{55}$, TTR Phe$^{78}$, vitronictin, poly Lysine, poly arginine, serum amyloid A, cystantin C, IgG kappa light chain, other amyloid peptides disclosed herein and amyloid peptides associated each amyloid disease disclosed herein may be used.

Peptides useful in the present invention may be obtained from natural sources, for example, purified from a naturally occurring source, or they may be manufactured. Methods of manufacture include any suitable method including, but not limited to, solid phase synthesis and heterologous gene expression.

The fact that the present antigen is common to amyloids of widely varying primary sequence Indicates that the epitope is formed from a specific three dimensional conformation of the polypeptide backbone referred to as a conformational epitope Solid phase synthesis and purification of peptides may be carried out by fluoren-9-ylmethoxy carbonyl chemistry using a continuous flow semiautomatic instrument as is described in D. Burdick et al. (1992) J Biol Chem 267, 546-54 the disclosure of which is incorporated herein by reference.

Briefly, the first Fmoc-amino acid is manually coupled to sulfamylbutyry-AM-PEGA resin (Novabiochem, San Diego, Calif.) in Dichloro methane(DCM). Diisopropylethylamine (DIEA) is added, the mixture is stirred for 20 min at room temperature, cooled to −10 to −20 C and ByBop (benzotriazol-1-yl-oxy-tris(pyrrolidino)-phosphonium hexafluorophosphate) is added. The mixture is stirred for 8 to 9 hours at −10 to −20° C. The coupling efficiency may be checked using the Kaiser test, which is well known in the art of peptide synthesis.

Acetylation may be performed using acetic anhydride. Amino acid chain elongation is by fluoren-9-ylmethoxy carbonyl chemistry using a continuous flow semiautomatic instrument. The peptide is washed with N-methyl-2-pyrrolidone 5× (NMP) 5.0 mL of NMP, 185 µL of i-Pr2EtN (1.1 mmol), and 400 µL of iodoacetonitrile (previously filtered through an alumina basic filter bed in the dark) in a synthesis vessel. The reaction mixture is then shaken for 24 h in the dark on a rotary plate. The resin is washed with 5× with NMP and 5×DMF followed by a wash using 5×CH$_2$Cl$_2$ and then dried. Resin is washed with 5×THF followed by the addition of THF and TMS-CH2N2 (50:50, v/v, hexane). After stirring for 2 h, the resin is washed with THF and DMF.

The resin is added to 120 µL of ethyl-3mercaptopropionate and the mixture shaken on a rotary plate for 24 h. The resin is filtered then washed with 3×3 ml DMF. The filtrate and washes are collected and rotary evaporated at 34° C.

The resulting peptides are deprotected using standard methods (TFA and scavengers), and purified by RP-HPLC. The purity may be checked by analytical RP-HPLC and electrospray mass spectrometry.

The peptides may also be produced by standard heterologous gene expression methods. For example, recombinant expression can be in bacteria, such as *E. coli*, or in yeast, insect cells or mammalian cells. Procedures for recombinant expression are described by Sambrook et al., Molecular Cloning: A Laboratory Manual (C. S. H. P. Press, NY 2d ed., 1989). In addition, many amyloid peptides including human insulin or lysozyme may be obtained from commercial sources.

The peptides useful in the present invention may be advantageously aggregated or conformationally constrained to form an epitope useful as described herein. In one useful embodiment, the peptides are associated with a surface for example, physically attached or chemically bonded to a surface in such a manner so as to allow for the production of an epitope which is recognized by the antibodies of the present invention.

For example, a C-terminal thioester may be attached to the peptides in a conventional manner as is known to those of ordinary skill in the field. For example, C-terminal thioesterification of the peptides by Fmoc chemistry may carried out essentially as described in Inginito, R. et al., (1999) Journal of the American Chemical Society 121, 11369-11374. C-terminal thioesterified peptides will readily attach to a surface such as a metallic surface.

The surface to which the peptides are associated with or attached to may be any suitable surface. For example the surface may be solid. The surface may include one or more of hydrocarbons, a polymer or polymers, plastic, glass, metal, ceramic or one or more biomolecules such as proteins, fats, nucleic acids and carbohydrates. More than one of these components may comprise the surface. For example, a particle may comprise a polymer coated with a metal. The surface may be flat or have a three dimensional shape such as a curved surface. In addition, the surface may be a particle. In one embodiment, oligomeric aggregate molecular mimics are produced using nanospheres. The nanospheres may be of any suitable size. For example, the diameter of the nanospheres may be in a range of about 0.01 nm to about 1 cm. In one useful embodiment, the nanospheres are about 5 nm in diameter.

In one particularly useful embodiment, gold nanospheres are used to produce molecular mimics. Briefly, the nanospheres may be incubated in a solution of 0.2 mg/ml of the C-terminal thioester peptide, pH (5.0-5.5) for 3 h followed by pH adjustment to 7.4 with 100 mM Tris pH 8.0 (0.2% sodium azide). After incubation for 6 h at room temperature, the molecular mimics are collected by centrifugation and washed three times with PBS pH 7.6 to remove unincorporated peptide and are then stored in 0.02% sodium azide at 4° C. Assembly of such a molecular mimic is shown in FIG. 1. This is but an example of a method for producing molecular mimics of the invention. Other methods of producing the mimics will be readily apparent to those of ordinary skill in the art.

The invention includes antibodies that recognize an epitope present on amyloid intermediates but do not recognize epitopes present on amyloid monomers, dimers, trimers or tetramers, or epitopes of mature amyloid fibrils or those of amyloid deposits which comprise amyloid peptides aggregated in an insoluble mass.

Antibodies of the present invention may be made by any suitable means. For example, the antibodies may be produced in laboratory animals. In one such case, New Zealand white rabbits, Balb/C, C57/Black6 mice or domestic dogs are injected with a quantity of molecular mimic produced as described above. The antigen is mixed with incomplete Freund's adjuvant, alum adjuvant or with no adjuvant (PBS only) prior to injection. For the first injection, equal parts antigen and adjuvant are used. For subsequent injections, the antigen is mixed with adjuvant and each injected, for example, at 2-week intervals. Animals may be injected subcutaneously in small increments of 0.1 mL per site in a checkerboard fashion on the scapular region.

The antigen is constrained in a conformation that results in the production and display on the solvent accessible surface of the antigen of the conformation-dependent epitope that is recognized by the antibody. Specifically, the attachment of the carboxyl terminus to the surface substrate maintains this region in close apposition to the surface, an arrangement that mimics the arrangement of the Aµ peptide in soluble oligomers [Garzon-Rodriguez, 2000 #6890]. The attachment of the carboxyl terminus to the solid support prevents the rearrangement of this region of the peptide that occurs during the structural transition of soluble oligomers to amyloid fibrils. In amyloid fibrils, the carboxyl terminus is freely mobile and found at the solvent accessible surface of the amyloid fibril [Garzon-Rodriguez, 2000 #6890][Torok, 2002 #8927][Antzutkin, 2003 #10555]. The attachment of the carboxyl terminus to the solid support also maintains a parallel alignment of the polypeptide chains and prevents the dissociation of the polypeptide into its monomeric or low MW, monomer, dimer, trimer and tetramers forms.

The preferred antibodies of the present invention remain bound during wash times of more than one hour and, thus, appear to exhibit relatively high binding affinity. In at least some of the antibodies of the present invention, the half time for dissociation is greater than one hour.

The antibody recognizes an epitope that is shared or common to soluble oligomers from a broad range of amyloidogenic peptides and proteins regardless of sequence. This epitope is absent or substantially reduced in its structure or accessibility in the low MW forms of the peptides and in the amyloid fibrils. The epitope consists of common structural and conformational features of the peptide, including but not limited to a specific conformation of the polypeptide backbone that is formed by many different protein and peptide sequences. The epitope recognized by the antibody is such that the binding of the antibody to the epitope substantially reduces or eliminates the toxicity of the soluble oligomers regardless of the protein or peptide sequence that display the epitope. It is to be understood, however, that this description of the inventions does not necessarily exclude antibodies that are specific for different sequences, as such antibodies are possible and they will bind to the same epitope on one peptide, but they may be sequence specific and not recognize all the other amyloids.

For serum collection, the IgG fraction may be affinity purified, for example, on Protein G-Sepharose beads, eluted, then dialyzed against PBS. The intermediate aggregate-specific antibodies may be purified by adsorption on the amyloid oligomeric intermediate molecular mimics produced as described above by mixing the molecular mimics with the IgG fraction and incubating for about 2 h, followed by washing. After elution, the antibody may be dialyzed against PBS stored in PBS containing 0.02% sodium azide at 4° C. or at −70° C.

Polyclonal serum produced by vaccination of rabbits, dogs or other animals with the molecular mimics disclosed herein is specific for amyloid peptide aggregate intermediates and is not detectably reactive with soluble low molecular weight or fibrillar amyloid species. See Example 4. Surprisingly, no anti-oligomer immunoreactivity against low molecular weight aggregates or fibrils is observed for the unfractionated serum indicating that the immune response to the molecular mimics is very specific. For example, antibodies produced against Aβ molecular mimics do not bind to Aβ low molecular weight aggregates or to Aβ fibrils, even after boosting the rabbits twelve times with Aβ molecular mimic.

Antibodies produced against Aβ peptide aggregate mimics are shown to bind to amyloid aggregate intermediates of all other amyloid types examined. See FIG. 6. In addition, these antibodies are shown to neutralize the toxicity of oligomeric forms of all toxic amyloids (i.e., amyloid intermediates) examined. See FIGS. 7, 8 and 9. The implication is that amyloid intermediates share a common structure. Therefore, the present invention contemplates that antibodies produced using a molecular mimic comprising amyloid peptides of one type will produce an antibody (e.g., a conformation dependent antibody) specific for other amyloid peptide intermediate types, for example, all amyloid peptide intermediate types. For example, it is contemplated that antibodies prepared from molecular mimics comprising-synuclein peptides will specifically react not only with -synuclein protofibrillar aggregate, but with oligomeric Intermediates of other amyloid oligomeric intermediate forms, for example, all other amyloid oligomeric intermediate forms.

Each of the following amyloid peptides have been shown to form amyloid peptide aggregates which produce a conformational epitope recognized by the antibodies of the present invention, for example, antibodies produced against Aβ peptide oligomeric intermediates. Some of these peptides are present in amyloid deposits of humans or animals having a disease characterized by the amyloid deposits. The present invention is not limited to the listed peptide or protein sequences or the specific diseases associated with some of the sequences. The present invention contemplates antibodies as described herein binding to other amyloid peptide aggregates or all other amyloid peptide aggregates. In particular, the present invention contemplates the application of methods and compositions of the present invention to other peptide or protein sequences which form amyloid precursor aggregates associated with other diseases.

```
A40
                                           (SEQ ID NO 1)
DAEFRHDSGYEVHHQKLVFF AEDVGSNKGA IIGLMVGGVV

A42
                                           (SEQ ID NO 2)
DAEFRHDSGY EVHHQKLVFF AEDVGSNKGA IIGLMVGGVV IA

Human IAPP
                                           (SEQ ID NO 3)
KCNTATCATQ RLANFLVHSS NNFGAILSST NVGSNTY Human Prion 106-126
                                           (SEQ ID NO 4)
           KTNMKHMAGA AAAGAVVGGL G
```

Stefani and coworkers (Bucciantini et al (2002) Nature 416, 507-511) have recently reported that amyloid peptide aggregates formed from non-disease-related proteins are inherently cytotoxic, suggesting that they may have a structure in common with disease related amyloid peptides. Non-disease related amyloid peptide aggregates comprising the following non-disease related amyloid peptides are also shown to bind to the antibodies of the present invention.

```
Poly glutamine synthetic peptide KK(Q40)KK
                                           (SEQ ID NO 5)
KKQQQQQQQQ QQQQQQQQQQ QQQQQQQQQQ QQQQQQQQQQ QQKK Human Lysozyme
                                           (SEQ ID NO 6)
     MKALIVLGLV LLSVTVQGKV FERCELARTL KRLGMDGYRG

SLANWMCLA  KWESGYNTRA TNYNAGDRST DYGIFQINSR
```

```
-continued
YWCNDGKTPG AVNACHLSCS ALLQDNIADA VACAKRVVRD

PQGIRAWVAW RNRCQNRDVR QYVQGCGV

Human Insulin
                                           (SEQ ID NO 7)
MALWMRLLPL LALLALWGPD PAAAFVNQHL CGSHLVEALY

LVCGERGFFY TPKTRREAED LQVGQVELGG GPGAGSLQPL

ALEGSLQKRG IVEQCCTSIC SLYQLENYCN

Human Transthyretin
                                           (SEQ ID NO 8)
MASHRLLLLC LAGLVFVSEA GPTGTGESKC PLMVKVLDAV

RGSPAINVAV HVFRKAADDT WEPFASGKTS ESGELHGLTT

EEEFVEGIYK VEIDTKSYWK ALGISPFHEH AEVVFTANDS

GPRRYTIAAL LSPYSYSTTA VVTNPKE

Human Alpha Synuclein
                                           (SEQ ID NO 9)
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

In addition, oligomeric intermediates formed from variants and fragments of wild type A 42, A 40 including, without limitation A 42 (A21G) Flemish mutation), A 42 (E22Q) Dutch mutation, A 42 (E22G) Arctic mutation, A 42 (D23N) Iowa mutation, A 40 (A21G) Flemish mutation), A 40 (E22Q) Dutch mutation, A 40 (E22G) Arctic mutation, A 40 (D23N) Iowa mutation, A 40 (E22Q &D23N) Dutch & Iowa mutations, A 3-42 (pGlu 3), A 3-40 (pGlu 3), A 8-42, A 17-42, A 1-16, A 3-11, A 25-35, A 4-16 (3 analogues, Cys[16] A 4-16, Ala' A 4-16, and Ala[10] A 4-16), His6 (SEQ ID NO: 10) A 40C40 (6 histidines appended to the amino terminus of AβC40) are recognized by the antibodies of the present invention. Other oligomeric intermediates recognized by antibodies of the invention include, without limitation, oligomeric intermediates formed from IAPP(C2A and C7A) where alanine is substituted for the naturally occurring cysteine in IAPP, Polyglutamine KKQ40KK (SEQ ID NO: 5. I or poly glutamine where the number of Q residues is greater than 32, Calcitonin, TTR and its mutants TTR Pro[55], TTR Phe[78], vitronictin, poly Lysine, poly arginine, serum amyloid A, cystantin C, IgG kappa light chain, oligomeric intermediates produced from other amyloid peptides disclosed herein and amyloid intermediates associated with amyloid diseases disclosed herein.

The present invention provides for amyloid disease therapeutics which induce a specific Immune response against amyloid oligomeric intermediates. These therapeutics include molecular mimics which comprise the conformational epitopes of aggregations of amyloid peptides and aggregations of variants of the peptides, aggregations of analogs and mimetics of amyloid peptides that induce and/or cross react with antibodies of the present invention, and antibodies or T-cells reactive with such antibodies. Induction of an immune response can be active as when an immunogen is administered to induce antibodies or T-cells reactive specifically reactive with amyloid peptide intermediates in a patient, or passive, as when an antibody is administered that itself specifically binds to amyloid peptide intermediates in the patient.

Analogs include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino adds or modifications of N or C terminal amino acids. Examples of unnatural amino acids are A-disubstituted amino acids,—alkyl amino acids, lactic acid, 4-hydroxyproline, carboxyglutamate, e-N,N, N-trimethyllysine, e-N-acetyllysine, O-phospgoserine, N-acetylserine, N-formylmethionine, 3-methylhistidine, 5-hydroxylysine, w-N-methylarginine.

Therapeutics also include aggregates of longer peptides or proteins that include, for example, an amyloid peptide, active fragment or analog together with other amino acids. For example, an Aβ peptide can be present as intact APP protein or a segment thereof, such as the C-100 fragment that begins at the N-terminus of Aβ and continues to the end of APP. Such polypeptides can be screened for preventative or therapeutic efficacy in animal models as described below. The Aβ peptide, analog, active fragment or other polypeptide can be administered in a form which will provide for an immune response against the three dimensional or conformational epitope which is not substantially present on low molecular weight oligomers or fibrils.

Therapeutics also comprise peptides and other compounds which do not necessarily have a significant amino acid sequence similarity with amyloid proteins but nevertheless will function as an antigen of the invention providing for an immune response against a conformational epitope of an amyloid oligomer intermediate. For example, any peptides and proteins forming -pleated sheets can be screened for suitability. Anti-idiotypic antibodies against monoclonal antibodies to amyloid intermediates or synthetic mimics of amyloid intermediates can also be used. Such anti-ld antibodies mimic the antigen and generate an immune response to it (see Essential Immunology (Roit ed., Blackwell Scientific Publications, Palo Alto, 6th ed.), p. 181).

Random libraries of peptides or other compounds can also be screened for suitability for use herein. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric -substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, for example, Devlin, WO 91/18980.

Any peptide aggregates, natural or synthetic, or other compounds of interest may be initially screened for suitability as an immunogen or antigen for use herein by determining the capacity of the aggregate or compound to bind to antibodies or lymphocytes (B or T) known to be specific for oligomeric intermediates. For example, initial screens can be performed with any polyclonal sera or monoclonal antibody to oligomeric intermediates.

Compounds identified by such screens may be further analyzed for capacity to induce antibodies or reactive lymphocytes to oligomeric intermediates. For example, multiple dilutions of sera can be tested on microtiter plates that have been precoated with an oligomeric intermediate mimic of the invention or purified oligomeric intermediates and a standard ELISA can be performed to test for reactive antibodies. Compounds can then be tested for prophylactic and therapeutic efficacy, for example, in transgenic animals predisposed to an amyloidogenic disease, as is understood in the art. Such animals include, for example, mice bearing a 717 mutation of APP described by Games et al., supra, and mice bearing a Swedish mutation of APP such as described by McConlogue et al., U.S. Pat. No. 5,612,486 and Hsiao et al., (1996) Science 274,99; Staufenbiel et al., Proc. Natl. Acad. Sci. USA (1997) 94, 13287-13292; Sturchler-Pierrat et al., Proc. Natl. Acad. Sci. USA 94, 13287-13292; Borchelt et al., Neuron (1997) 19,939-945. The same screening approach can be used on other potential therapeutics including those described above.

Therapeutics of the invention also include antibodies that specifically bind to oligomeric intermediates. Such antibodies can be monoclonal or polyclonal. In one useful embodiment, the antibodies bind to a conformational epitope. The production of non-human monoclonal antibodies, for example, murine or rat, can be accomplished by, for example, immunizing the animal with an oligomeric intermediate mimic of the invention. Also contemplated is immunizing the animal with a purified amyloid intermediate.

Humanized forms of mouse antibodies of the invention can be generated by linking the CDR regions of non-human antibodies to human constant regions by recombinant DNA techniques. See Queen et al., Proc. Natl. Acad. Sci. USA 86, 10029-10033 (1989) and WO 90/07861 (incorporated by reference for all purposes).

Human antibodies may be obtained using phage-display methods. See, for example, Dower et al., WO 91/17271 and McCafferty et al., WO 92/01047. In these methods, libraries of phage are produced in which members display different antibodies on their outer surfaces. Phage displaying antibodies with a desired specificity are selected by affinity enrichment. Human antibodies against oligomeric intermediates may also be produced from non-human transgenic mammals having transgenes encoding at least a segment of the human immunoglobulin locus and an inactivated endogenous immunoglobulin locus. See, for example, Lonberg et al., WO93/12227 (1993); Kucherlapati, WO 91/10741 (1991) (each of which is incorporated by reference in its entirety for all purposes). Human antibodies can be selected by competitive binding experiments, or otherwise, to have the same epitope specificity as a particular mouse antibody. Such antibodies are particularly likely to share the useful functional properties of the mouse antibodies.

Human polyclonal antibodies can also be provided in the form of serum from humans immunized with an immunogen of the invention. Optionally, such polyclonal antibodies can be concentrated by affinity purification using, for example, an immunogen of the invention as an affinity reagent.

Human or humanized antibodies can be designed to have IgG, IgD, IgA and IgE constant region, and any isotype, including IgG1, IgG2, IgG3 and IgG4. Antibodies can be expressed as tetramers containing two light and two heavy chains, as separate heavy chains, light chains, as Fab, Fab' F(ab')$_2$ and Fv, or as single chain antibodies in which heavy and light chain variable domains are linked through a spacer.

Therapeutics for use in the present methods may also include T-cells that bind to amyloid oligomeric intermediates. For example, T-cells may be activated against an Intermediate by expressing a human MHC class I gene and a human -2-microglobulin gene from an insect cell line, whereby an empty complex is formed on the surface of the cells and can bind to oligomeric intermediate antigen. T-cells contacted with the cell line may become specifically activated against the antigen. See Peterson et al., U.S. Pat. No. 5,314,813. Insect cell lines expressing an MHC class II antigen can similarly be used to activate CD4 T cells.

In certain instances it may be desirable to link an immunogen of the invention to a suitable carrier. Suitable carriers include serum albumins, keyhole limpet hemocyanin, immunoglobulin molecules, thyroglobulin, ovalbumin, tetanus toxoid, or a toxoid from other pathogenic bacteria, such as *diphtheria, E. coli, cholera,* or *H. pylori*, or an attenuated toxin derivative. Other carriers for stimulating or enhancing an immune response include cytokines such as IL-1, IL-1 and β peptides, IL-2, INF, IL-10, GM-CSF, and chemokines, such as M1P1 and P and RANTES. Immunogenics can also be linked to peptides that enhance transport across tissues, as described in O'Mahony, WO 97/17613 and WO 97/17614.

Immunogens of the invention can be linked to carriers by chemical crosslinking. Techniques for linking an immunogen to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the e-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Peptides included in immunogens of the invention can also be expressed as fusion proteins. The peptide can be linked at the amino terminus, the carboxyl terminus or internally or to the carrier. For example, the peptides may be fused with carriers or with any useful peptide or protein sequence.

Patients amenable to treatment include individuals at risk of disease but not showing symptoms, as well as patients presently showing symptoms. In the case of certain amyloid diseases including AD, virtually anyone is at risk of suffering from the disease.

Therefore, the present compositions can be administered prophylactically, for example, by a vaccine, to the general population without any assessment of the risk of the subject patient. The present methods are especially useful for individuals who do have a known genetic risk of an amyloid disease, for example, AD. Such individuals may include those having relatives who have experienced an amyloid disease, and those whose risk is determined by analysis of genetic or biochemical markers or who exhibit symptoms or prodromes indicative of the potential for development of, or the actual presence of, such diseases. For example, genetic markers of risk toward AD include mutations in the APP gene, particularly mutations at position 717 and positions 670 and 671 referred to as the Hardy and Swedish mutations respectively (see Hardy, TINS, supra). Other markers of risk for AD are mutations in the presenilin genes, PS1 and PS2, and ApoE4, family history of AD, hypercholesterolemia or atherosclerosis.

Symptoms of amyloid disease are apparent to a physician of ordinary skill. For example, individuals presently suffering from Alzheimer's disease can be recognized from characteristic dementia, as well as the presence of risk factors described above. In addition, a number of diagnostic tests are available for identifying individuals who have amyloid diseases. For example, in the case of AD these include measurement of CSF tau and A42 levels. Elevated tau and decreased A42 levels signify the presence of AD.

In asymptomatic patients, treatment can begin at any age, for example, at the age of 10, 20, 30, 40, 50, 60 or 70. Treatment may entail one or more doses, for example, multiple dosages over a period of time. Treatment can be monitored by assaying antibody, or activated T-cell or B-cell responses to the therapeutic (for example, oligomeric intermediate mimic) or assaying the levels of protofibrillar aggregate present, each over time. In one embodiment, treatment by administering a single therapeutic of the invention, such as a single immunogen of the invention, may serve as a treatment for or preventive measure against more than one amyloid disease, for example all amyloid diseases.

In prophylactic applications, compositions of the invention or medians are administered to a patient susceptible to, or otherwise at risk of, a particular disease in an amount sufficient to eliminate or reduce the risk or delay the outset of the disease. In therapeutic applications, compositions or medians are administered to a patent suspected of, or already suffering from such a disease in an amount sufficient to cure, or at least partially arrest, the symptoms of the disease and its complications. An amount adequate to accomplish this is defined as a therapeutically-or pharmaceutically-effective dose. In both prophylactic and therapeutic regimes, therapeutics are usually administered in several dosages until a sufficient immune response has been achieved. Typically, the immune response is monitored and repeated dosages are given if the immune response starts to fade.

Effective doses of the compositions of the present invention, for the treatment of the above described conditions vary depending upon many different factors, including means of administration, target site, physiological state of the patient, whether the patient is human or animal, other medications administered, and whether treatment is prophylactic or therapeutic. Usually, the patient is a human, but in some diseases, such as mad cow disease, the patient can be a nonhuman mammal, such as a bovine or in the case of Alzheimer's disease, the patient may be a dog. Treatment dosages need to be titrated to optimize safety and efficacy. The amount of immunogen depends on whether adjuvant is also administered, with higher dosages being required in the absence of adjuvant. The amount of an immunogen for administration sometimes varies from about 1 μg to about 500 μg per patient and more usually from about 5 μg to about 500 μg per injection for human administration. Occasionally, a higher dose of about 1 mg to about 2 mg per injection is used. Typically about 10 μg, about 20 μg, about 50 μg or about 100 μg is used for each human injection. The timing of injections can vary significantly from once a day, to once a year, to once a decade. On any given day that a dosage of immunogen is given, the dosage is greater than 1 μg per patient and usually greater than 10 μg per patient if adjuvant is also administered, and greater than 10 μg per patient and usually greater than 100 per patient in the absence of adjuvant. The mass amount of peptide present in the dosage may be used to calculate the quantities of therapeutic used.

One typical regimen consists of an immunization followed by booster injections at 6 weekly Intervals. Another regimen consists of an immunization followed by booster injections 1,2 and 12 months later. Another regimen entails an injection every two months for life. Alternatively, booster injections can be on an irregular basis as indicated by monitoring of immune response.

For passive immunization with an antibody, the dosage ranges from about 0.0001 mg/kg of body weight to about 100 mg/kg of body weight, and more usually about 0.01 mg/kg of body weight to about 5 mg/kg of body weight of the host.

Therapeutics for inducing an immune response can be administered by any suitable means, for example, parenteral, topical, intravenous, oral, subcutaneous, intraperitoneal, intranasal or intramuscular means for prophylactic and/or therapeutic treatment. The most typical route of administration is subcutaneous although others can be equally effective. The next most common is intramuscular injection. This type of injection is most typically performed in the arm or leg muscles. Intravenous injections as well as intraperitoneal injections, intraarterial, intracranial, or intradermal injections may also be effective in generating an immune response. In some methods, therapeutics are injected directly into a particular tissue where deposits have accumulated or may accumulate.

Compositions of the invention can optionally be administered in combination with other agents that are at least partly effective in treatment of amyloidogenic disease. In the case of Alzheimer's and Down's syndrome, in which amyloid deposits occur in the brain, therapeutics of the invention can also be administered in conjunction with other agents that increase passage of the compositions of the invention across the blood-brain barrier.

Immunogenic agents of the invention, such as peptides, are sometimes administered in combination with an adjuvant. A variety of adjuvants can be used in combination with an immunogen of the invention to elicit an immune response. Preferred adjuvants augment the intrinsic response to an immunogen without causing conformational changes in the immunogen that affect the qualitative form of the response. Preferred adjuvants include alum, 3 de-O-acylated monophosphoryl lipid A (MPL) (see GB 2220211). QS21 is a triterpene glycoside or saponin isolated from the bark of the Quillaja Saponaria Molina tree found in South America (see Kensil et al., in Vaccine Design: The subunit and Ajuvant Approach (eds. Powell & Newman, Plenum Press, NY, 1995); and U.S. Pat. No. 5,057,540). Other adjuvants are oil in water emulsions, such as squalene or peanut oil, optionally in combination with immune stimulants, such as monophosphoryl lipid A. See, for example, Stoute et al., N. Engl. J. Med. (1997) 336, 86-91. Another useful adjuvant is CpG described in Bioworld Today, Nov. 15, 1998. Alternatively, an immunogen can be coupled to an adjuvant. For example, a lipopeptide version of the immunogen may be prepared by coupling palmitic acid or other lipids directly to the N-terminus of one or more peptides which comprise an immunogen of the invention, as described for hepatitis B antigen vaccination in Livingston, J. Immunol. (1997) 159, 1383-1392. However, such coupling should not substantially change the conformation of the peptides comprising the immunogen so as to affect the nature of the immune response thereto. Adjuvants can be administered as a component of a therapeutic composition with an active agent or can be administered separately, before, concurrently with, or after administration of the therapeutic.

A preferred class of adjuvants is aluminum salts (alum), such as aluminum hydroxide, aluminum phosphate, aluminum sulfate. Such adjuvants can be used with or without other specific immunostimulating agents such as MPL or 3-DMP, QS21, polymeric or monomeric amino acids such as polyglutamic acid or polylysine.

Another class of adjuvants is oil-in-water emulsion formulations. Such adjuvants can be used with or without other specific immunostimulating agents such as muramyl peptides (for example, N-acetylmuramyl-L-threonyl-D-isoglutamine (thr-MDP), -acetyl-normuramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80 and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80.5% pluroinic-blocked polymer L121, and thr-MDP, either microfluidized into a submicron emulsion or vortexed to generate a larger particle size emulsion, and (c) Ribi™ adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™)

Another class of preferred adjuvants is saponin adjuvants, such as Stimulons (QS21, Aquila, Worcester, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins, for example, IL-1, IL-2, and IL-12, macrophage colony stimulating factor (M-CSF), tumor necrosis factor (TNF) and/or chemokines such as CXCL10 and CCL5.

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Optionally, two or more different adjuvants can be used simultaneously. Preferred combinations include alum with MPL, alum with QS21, MPL with QS21, and alum, QS21 and MPL together. Also, Incomplete Freund's adjuvant can be used (Chang et al., Advanced Drug Delivery Reviews 32,173-186 (1998)), optionally in combination with any of alum, QS21, and MPL and all combinations thereof.

Compositions of the invention are often administered as pharmaceutical compositions comprising a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. However, some reagents suitable for administration to animals, such as complete Freund's adjuvant are not typically included in compositions for human use.

Pharmaceutical compositions can also include large, slowly metabolized macromolecules such as proteins, polysaccharides, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of the invention can be administered as injectable dosages of a solution or suspension of the substance in a physiologically acceptable diluent with a pharmaceutical carrier which can be a sterile liquid such as water oils, saline, glycerol, or ethanol.

Auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Compositions may be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. See Langer, Science (1990) 249, 1527 and Hanes, Advanced Drug Delivery Reviews (1997) 28, 97-119. The compositions of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient In the range of 0.5% to about 10%, for example, about 1% to about 2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and may contain about 10% about 95% of active ingredient, for example, about 25% to about 70%.

Topical application can result in transdermal or intradermal delivery. Topical administration can be facilitated by co-administration of the composition with cholera toxin or detoxified derivatives or subunits thereof or other similar bacterial toxins. See Glenn et al., Nature (1998) 391, 851. Co-administration can be achieved by using the components as a mixture or as linked molecules obtained by chemical crosslinking or expression as a fusion protein.

Alternatively, transdermal delivery can be achieved using a skin path or using transferosomes. See for example, Paul et al., Eur. J. Immunol. (1995) 25, 3521-24; Cevc et al., Biochem. Biophys. Acta (1998) 1368, 201-15.

The invention provides methods of detecting an immune response against amyloid oligomeric intermediates in a patient suffering from or susceptible to amyloid diseases such as AD. The methods are particularly useful for monitoring a course of treatment being administered to a patient. The methods can be used to monitor both therapeutic treatment on symptomatic patients and prophylactic treatment on asymptomatic patients.

Some methods entail determining a baseline value of an immune response in a patient before administering a dosage of composition, and comparing this with a value for the immune response after treatment. A significant increase (i.e., greater than the typical margin of experimental error in repeat measurements of the same sample, expressed as one standard deviation from the mean of such measurements) in value of the immune response signals a positive treatment outcome (i.e., that administration of the composition has achieved or augmented an immune response). If the value for immune response does not change significantly, or decreases, a negative treatment outcome is indicated. In general, patients undergoing an initial course of treatment with a composition are expected to show an increase in immune response with successive dosages, which eventually reaches a plateau. Administration of composition is generally continued while the immune response is increasing.

Attainment of the plateau is an indicator that the treatment can be discontinued or reduced in dosage or frequency.

In other methods, a control value (i.e., a mean and standard deviation) of immune response is determined for a control population. Typically the Individuals in the control population have not received prior treatment. Measured values of immune response in a patient after administering a therapeutic composition are then compared with the control value. A significant increase relative to the control value (for example, greater than one standard deviation from the mean) signals a positive treatment outcome. A lack of significant increase or a decrease signals a negative treatment outcome.

Administration of composition is generally continued while the immune response is increasing relative to the control value.

As before, attainment of a plateau relative to control values in an indicator that the administration of treatment can be discontinued or reduced in dosage or frequency.

In other methods, a control value of immune response (for example, a mean and standard deviation) is determined from a control population of individuals who have undergone treatment with a therapeutic composition and whose immune responses have plateaued in response to treatment. Measured values of immune response in a patient are compared with the control value. If the measured level in a patient is not significantly different (for example, more than one standard deviation) from the control value, treatment can be discontinued. If the level in a patient is significantly below the control value, continued administration of composition is warranted. If the level in the patient persists below the control value, then a change in treatment regime, for example, use of a different adjuvant may be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (e.g., greater than a typical margin of error in repeat measurements of the same sample) is an indication that treatment can be resumed. Alternatively, the value measured in patient can be compared with a control value (mean plus standard deviation) determined in population of patients after undergoing a course of treatment.

Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (e.g., more than a standard deviation) is an indicator that treatment should be resumed in a patient.

The tissue sample for analysis is typically blood, plasma, serum, mucus or cerebral spinal fluid from the patient. The sample may be analyzed for indicia of an immune response to an amyloid peptide aggregate or an amyloid peptide aggregate mimic. The immune response can be determined from the presence of, for example, antibodies or T-cells that specifically bind to an amyloid peptide aggregate or amyloid peptide aggregate mimic. ELISA methods of detecting antibodies specific to compositions are described in the Examples section.

The invention further provides diagnostic kits for performing the diagnostic methods described above. Typically, such kits contain a composition that specifically binds to antibodies to oligomeric intermediates or reacts with T-cells specific for oligomeric intermediates. The kit can also include a label. For detection of antibodies to amyloid peptide aggregates, the label is typically in the form of labelled anti-idiotypic antibodies. For detection of antibodies, the composition can be supplied prebound to a solid phase, such as to the wells of a microtiter dish. For detection of reactive T-cells, the label can be supplied comprising $^3$H-thymidine to measure a proliferative response. Kits also typically contain directions for use of the kit. The directions may also include a chart or other correspondence regime correlating levels of measured label with levels of antibodies to oligomeric intermediates or T-cells reactive with oligomeric intermediates.

EXAMPLES

Example 1

Molecular mimics of amyloid peptide aggregates were synthesized as follows.
Peptide Synthesis:

Solid phase synthesis and purification of A40 (SEQ ID NO 1), A42 (SEQ ID NO 2), IAPP (SEQ ID NO 3) and human prion 10-6126 (SEQ ID NO 4) were was carried out by fluoren-9-ylmethoxy carbonyl chemistry using a continuous flow semiautomatic instrument as described previously by D. Burdick et al. (1992) J Biol Chem 267, 546-54. C-terminal thioester by Fmoc chemistry was carried out essentially as described in Inginito, R. et al., (1999) Journal of the American Chemical Society 121, 11369-11374.

For each peptide, the first amino acid was manually coupled to the sulfamylbutyry-AM-PEGA resin (Novabiochem, San Diego, Calif.), 1 g of resin in 10 mL of Dichloro methane(DCM), 5 equivalents of the first amino acid was added (Fmoc-Ala-OH for A42), (Fmoc-Val-OH for A40), and (Fmoc-Tyr(t-But)-OH for IAPP), followed by the addition of 10 equivalents of Diisopropylethylamine (DIEA). The mixture was stirred for 20 min at room temperature, then cooled to (−10 to −20 C). 4.7 equivalents of ByBop (benzotriazol-1-yl-oxy-tris(pyrrolidino)-phosphonium hexafluorophosphate) was added and the mixture was stirred for 8 to 9 hours at −10 to −20° C. The coupling efficiency was checked using the Kaiser test, which is well known in the art of peptide synthesis, and the substitution level was found to be around 0.18- to 0.20 mmole/g, as determined using the Fmoc cleavage method. Acetylation was performed using acetic anhydride. The amino acid chain was elongated by fluoren-9-ylmethoxy carbonyl chemistry using a continuous flow semiautomatic instrument. 100 mg of peptide was washed with N-methyl-2-pyrrolidone 5× (NMP) 5.0 mL of NMP, 185 μL of i-Pr2EtN (1.1 mmol), and 400 μL of iodoacetonitrile (previously filtered through an alumina basic filter bed in the dark) in a synthesis vessel. The reaction mixture was shaken for 24 h in the dark on a rotary plate. The resin was washed with 5× with NMP and 5×DMF followed by a wash using 5×CH2Cl2 and then dried. 100 mg of resin was washed with 5×THF followed by the addition of 2.7 mL THF. 2.7 mL of TMS-CH2N2 (50:50, v/v, hexane) was then added. After stirring for 2 h, the resin was washed with 5×5 mL THF and 5×5 mL DMF.

The resin was added to 120 μL of ethyl-3-mercaptopropionate and the mixture was shaken on a rotary plate for 24 h. The resin was filtered then washed with 3×3 ml DMF. The filtrate and washes were collected, rotary evaporated at 34° C. The yields were about 60%.

The resulting peptides were deprotected using standard methods (TFA and scavengers), and purified by RP-HPLC. The purity was checked by analytical RP-HPLC and electrospray mass spectrometry.

Human insulin, lysozyme, Polyglutamine KKQ40KK (SEQ ID NO: 5) and -synuclein were obtained from commercial or other sources.

A C-terminal thioester was attached to each of these synthesized and commercial peptides in a conventional manner.
Colloidal Gold Amyloid Oligomer Molecular Mimic Assembly:

Colloidal gold nanospheres (mean diameter of 5.3 nm) were purchased from Ted Pella, Inc. and washed with 1 M HCL followed by three washings in distilled water. The gold nanospheres were incubated in a solution of 0.2 mg/ml of the C-terminal thioester peptide, pH (5.0-5.5) for 3 h. The pH was then adjusted to 7.4 with 100 mM Tris pH 8.0 (0.2% sodium azide).

After incubation for 6 h at room temperature, the antigen was collected by centrifugation at 30,000×G at 4° C. for 30 min, washed three times with PBS pH 7.6 to remove unincorporated peptide and then dispersed in 0.02% sodium azide. The resulting micelle molecular mimics were analyzed by atomic force microscopy (AFM), circular dichroism spectroscopy, thioflavin T fluorescence, bis-ANS fluorescence, and UV/visible spectroscopy to confirm that the peptide monolayer on the gold has the same secondary structure and conformation as the oligomeric amyloid intermediates display in solution. The solution was stored at 4° C.

Assembly of a molecular mimic is shown in FIG. 1.

Example 2

Production of antibodies to colloidal gold amyloid oligomer molecular mimics was performed as follows.

New Zealand white rabbits, Balb/C, C57/Black6 mice and domestic dogs were injected with a quantity of a molecular mimic produced as described in Example 1 corresponding to about 08. to about 1.0 mg of Aβ peptide. The gold conjugated antigen was mixed with incomplete Freund's adjuvant, alum adjuvant or with no adjuvant (PBS only) prior to injection. The rabbits were immunized with 1 mL of antigen (0.08-0.1 mg of peptide per rabbit, dialyzed against PBS at 4° C., overnight). For the first injection, equal parts antigen and complete Freund's adjuvant were used. For the subsequent 11 injections, the antigen was mixed with incomplete Freund's adjuvant and each were injected at 2-week intervals. Animals were injected subcutaneously in small increments of 0.1 mL per site in a checkerboard fashion on the scapular region.

Serum was collected by venipuncture. The IgG fraction was affinity purified on Protein G-Sepharose beads, eluted in 0.2 M glycine, pH 2.2, neutralized with Tris buffer to pH 7.4 and then dialyzed against PBS, pH 7.4. The intermediate aggregate-specific antibodies (termed Oligomer antibodies) were purified by adsorption on the amyloid oligomeric intermediate molecular mimics by mixing the molecular mimics with the IgG fraction and incubating for 2 h, followed by washing. The oligomeric intermediate specific antibody was eluted in 0.2 M glycine, pH 2.2, followed by neutralization and dialysis against PBS. The antibody was stored in PBS containing 0.02% sodium azide as preservative at 4° C. or at −70° C.

The polyclonal serum produced by vaccination of rabbits with the molecular mimics is specific for the amyloid peptide aggregate intermediates and is not detectably reactive with soluble low molecular weight or fibrillar Aβ species (see Example 4). Surprisingly, no anti-oligomer immunoreactivity against low molecular weight Aβ or Aβ fibrils was observed for the unfractionated serum even after boosting the rabbits twelve times, indicating that the immune response to the molecular mimics is very specific.

Example 3

Production of monomeric or low molecular weight aggregates, oligomeric intermediates and mature amyloid fibrils is described.
Preparation of Aβ Monomer and Low Molecular Weight Aggregates:

Monomeric peptides and low molecular weight aggregates were prepared by dissolving 1.0 mg Aβ in 400 μL HFIP at room temperature. 100 μL of the resulting Aβ solution was added to 900 μL DD H$_2$O in a siliconized Eppendorf tube. After 10-20 min incubation at room temperature, the samples were centrifuged for 15 min at 14,000×G and the supernatant fraction (pH 2.8-3.5) was transferred to a new siliconized tube and subjected to a gentle stream of N$_2$ for 5-10 min to evaporate the HFIP. The samples were then used immediately or fractionated by gel permeation to remove any fibrils or oligomeric intermediates.
Preparation of A β Oligomeric Intermediates:

Amyloid peptide aggregates were prepared by dissolving 1.0 mg Aβ in 400 μL HFIP for 10-20 min at room temperature. 100 μL of the resulting Aβ solution was added to 900 μL DD H$_2$O in a siliconized Eppendorf tube. After 10-20 min incubation at room temperature, the samples were centrifuged for 15 min at 14,000×G and the supernatant fraction was transferred to a new siliconized tube and subjected to a gentle stream of N$_2$ for 5 to 10 min to evaporate the HFIP. The samples were stirred at 500 RPM using a Teflon coated micro stir bar for 24 to 48 h at 22° C. 10 μl aliquots were taken at 6 to 12 h intervals for observation by AFM or EM. In order to prepare highly pure samples of intermediates residual trifluoroacetate ions are removed by lyophilization in 1 mM HCl followed by lyphilization in 50% acetonitrile.

The time of stirring required to obtain an optimum level of intermediates depends on subtle factors, which will be apparent to those of ordinary skill in the art, including the speed of stirring and the peptide concentration. The highest level of intermediates for Aβ was recovered after between 6 hrs and 3 days of stirring.

The amount of oligomeric intermediates and monomer or low molecular weight aggregates was monitored carefully using a Toso Haas TSK 300 gel permeation column or Suparose HR75 FPLC column. The intermediate was recovered at or near the void volume of the columns from the monomeric an low molecular weight Aβ that elutes at or near the included volume of the column.

Purification of the intermediates from fibrils is done by centrifugation at 100,000×G for 1 h. Monomeric or low molecular weight aggregates are removed by application of the supernatant to a gel permeation chromatography column. Intermediates are eluted near the void volume of the column and the monomer and low molecular weight aggregates elute near the included volume and are discarded.
Preparation of Protofibrils:

Spherical oligomers were prepared as described above, then an equal volume of PBS pH 7.4 was added and stirred for 24 hrs producing curved strings of spherical oligomers.
Preparation of Annular Protofibrils:

For the preparation of annular protofibrils, oligomeric intermediates were prepared as described above. The sample is subjected to vigorous stirring while drying by slow evaporation. To obtain substantially the same result, a few drops (less than 5% of the total volume) of hexane are added while the sample is stirring. This is done 10 times with a 5 min stir period for each addition.
Preparation of Fibrils:

Fibrils were prepared under three different conditions, water (pH 3.8 to 4.2), 10 mM Tris (pH 7.4), and 50 mM Tris 100 mM NaCl (pH 7.4), each containing 0.02% sodium azide. The final peptide concentration of Aβ was 0.3 to 0.5 mg/ml (80-125 μM). The samples were stirred with a Teflon coated micro stir bar at 500 rpm at room temperature for 6 to 9 days. Fibril formation was monitored by thioflavin T fluorescence and UV light scattering. Once fibril formation was complete, the solutions were centrifuged at 14,000×G for 20 min, the fibril pellet was washed 3× with the doubly distilled water and then resuspended in the desired buffer. The presence of mature fibril morphology and the absence of spherical oligomeric intermediates and protofibrils was verified by AFM or negative stain EM.

Example 4

The specificity of the anti-oligomer aggregate antibody was examined by screening lysates of SHSY5Y cells for cellular proteins that react with anti-oligomer antibody using dot blot analyses and ELISA assays.
Dot Blot Assay Monomeric or low molecular weight aggregates, oligomeric intermediates and amyloid fibrils were prepared as describe in Example 3 and were each dissolved in DD H$_2$0 at a concentration of 0.5 mg/ml immediately before use. 2 μl of each sample was applied to a nitrocellulose membrane. The membrane was blocked with 10% non-fat milk in Tris-buffered saline (TBS) containing 0.01% Tween 20 (TBS-T), at room temperature for 1 h. The membrane was washed three times for 5 min each with TBS-T and then incubated for 1 hr at room temperature with the affinity-purified anti-oligomer antibody (0.1 μg/ml in 3% BSA in TBS-T) or serum (diluted 1:1,000 in 3% BSA TBS-T). The concentration of Tween 20 is 10-fold lower than is normally used, because higher concentrations of detergent are shown to interfere with the detection of amyloid peptide aggregates by anti-oligomer. The membranes were washed three times for 5 min each with TBS-T, incubated with horseradish peroxidase-conjugated anti-rabbit IgG (Promega) diluted 1:10,000 in 3% BSA/TBS-T and incubated for 1 hour at room temperature. The blots were washed three times with TBS-T and developed with ECL chemiluminescence kit from Amersham-Pharmacia (Piscataway, N.J.). The same membrane was stripped by incubating for 45 min at 65° C. in stripping buffer (100 mM 2-mercaptoethanol, 2% SDS, 62.5 mM Tris-HCl, pH6.7), washed 5 times for 5 min with TBS-T, blocked with 10% non-fat milk and immunodetected with 6E10, as described above for anti-oligomer. 6E10 is a well know monoclonal antibody which detects amino acid residues 1-17 of human beta amyloid peptide.

Figure 2:
FIG. 2 shows the result of a dot blot assay where Aβ low molecular weight oligomers, Aβ high molecular weight oligomers and Aβ fibrils are spotted to a nitrocellulose membrane and are probed with anti-oligomer antibody and 6E10.

The following were applied to a nitrocellulose membrane and probed with anti-oligomer aggregate (anti-Oligo.) as shown in FIG. 2:
1-soluble A40 oligomers aggregate intermediates;
2-soluble low molecular weight A40; and
3-A40 fibrils.

It can be seen in FIG. 2 that anti-oligomer only recognizes the soluble aggregate intermediates, while 6E10 recognizes all species of A.

ELISA Assay

Samples were applied to a 96 well plate and analysed by ELISA using anti-oligomer aggregate antiserum produced as described in Example 2. Assays for soluble low molecular weight A40 (▲), soluble A40 oligomers (○), A40 fibril (■) are shown in FIG. 3.

Samples were diluted in coating buffer (0.1 M sodium bicarbonate, pH 9.6) and between 0 and 100 ng of each amyloid type in 100 µl of buffer was added to separate wells of 96-well microplates. The plates were incubated for 2 hours at 37° C., washed three times with PBS containing 0.01% Tween 20, PBS-T and then blocked for 2 h at 37° C. with 3% BSA TBS-T. The BSA used was IgG free (Sigma). The plates were then washed three times with PBS-T and 100 µl of anti-oligomer (1:10,000 dilution in 3% BSA/TBS-T) was added and incubated for 1 hour at 37° C. The plates were washed three times with PBS-T and 100 µl horseradish peroxidase-conjugated anti-rabbit IgG (Promega diluted 1:10, 000 in 3% BSA TBS-T) was added followed by incubation for 1 hour at 37° C. The plates were washed three times with PBS-T and developed using 3,3',5,5'-tetramethylbenzidine (TMB, KPL Gaitherburg, Md.). The reaction was stopped with 100 µL 1 M HCl and the plates were read at 450 nm.

Figure 3:
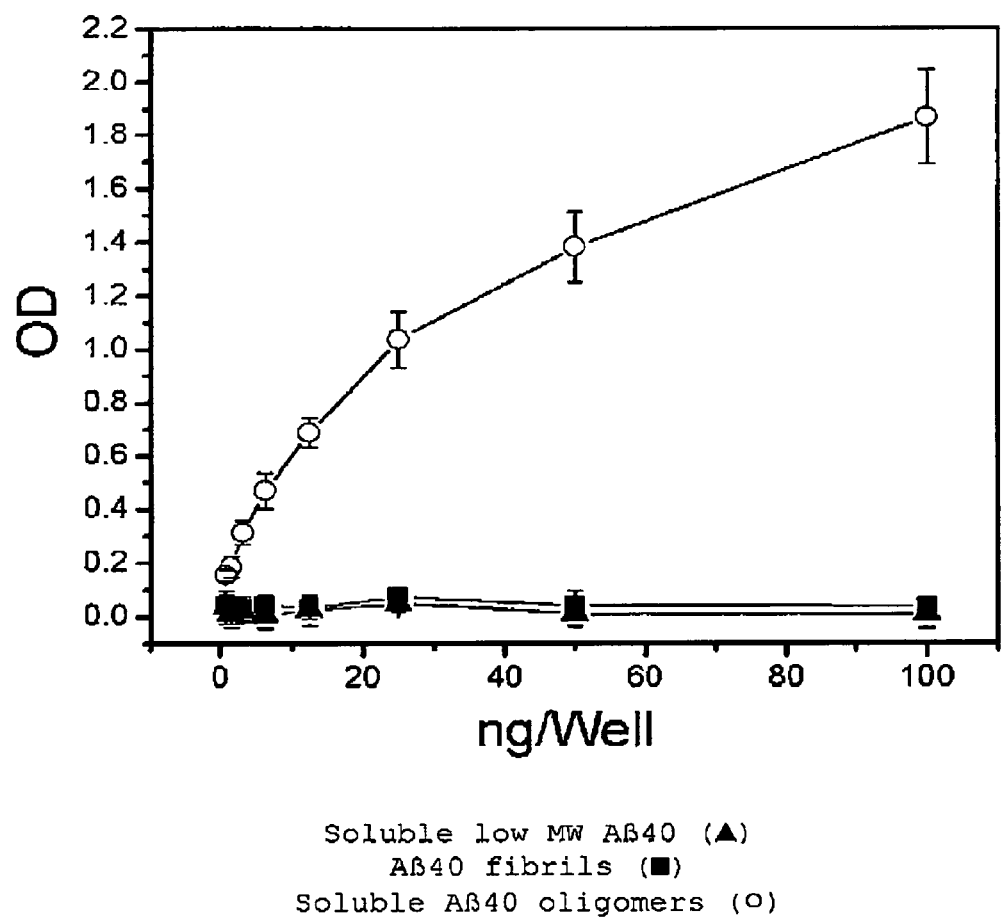
FIG. 3 shows the results of an ELISA assay where Aβ low molecular weight oligomers, Aβ high molecular weight oligomers and Aβ fibrils are analyzed for anti-oligomer specificity.

FIG. 3 shows that only the amyloid peptide aggregate A40 intermediates are recognized by anti-oligomer serum, while the soluble low molecular weight A40 and A40 fibrils give only background values.

Example 5

Kinetics of anti-oligomer immunoreactivity during fibrillogenesis was analysed by time point dot blot assay (FIG. 4).

Spherical aggregates are initially absent from freshly solubilized solutions of denatured Aβ peptide and evolve over time. In addition, spherical oligomer formation is known to precede formation of the curvilinear strings or protofibrils. See, for example, Harper et al (1999) Biochemistry 38 8972.

FIG. 4 shows a time point, dot blot assay in which A40 and A42 solutions were dissolved in HFIP, diluted to 56 µM Aβ and incubated in 100 mM NaCl, 50 mM Tris, pH 7.4 at 25° C. with stirring. At the times indicated, aliquots were applied to a nitrocellulose membrane and probed with anti-oligomer antibody (upper panel) and then stripped and re-probed with 6E10 (lower panel).

For A42, immunoreactivity is observed at 6 h and is maximal between 24 and 168 h. At 332 h, immunoreactivity is lost. The kinetics for A40 are similar to that of A42 except that intermediate formation is delayed by approximately 18-24 h which is consistent with previous observations that A42 forms oligomers faster than A40. The samples were examined by electron microscopy to determine the morphology during the this time course experiment. It was confirmed that at the early times of immunoreactivity, the samples contain predominantly spherical oligomers, while at later times the elongated "protofibrils" predominate. This observation indicates that the protofibrillar and less developed intermediate amyloid forms display the same conformational epitope recognized by anti-oligomer.

Example 6

Peptide aggregation size dependence for the appearance of the anti-oligomer aggregate epitope was examined by fractionating amyloid peptide aggregates by size-exclusion chromatography as described in Soreghan et al (1994) J Biol Chem 269 28551.

Figure 5:
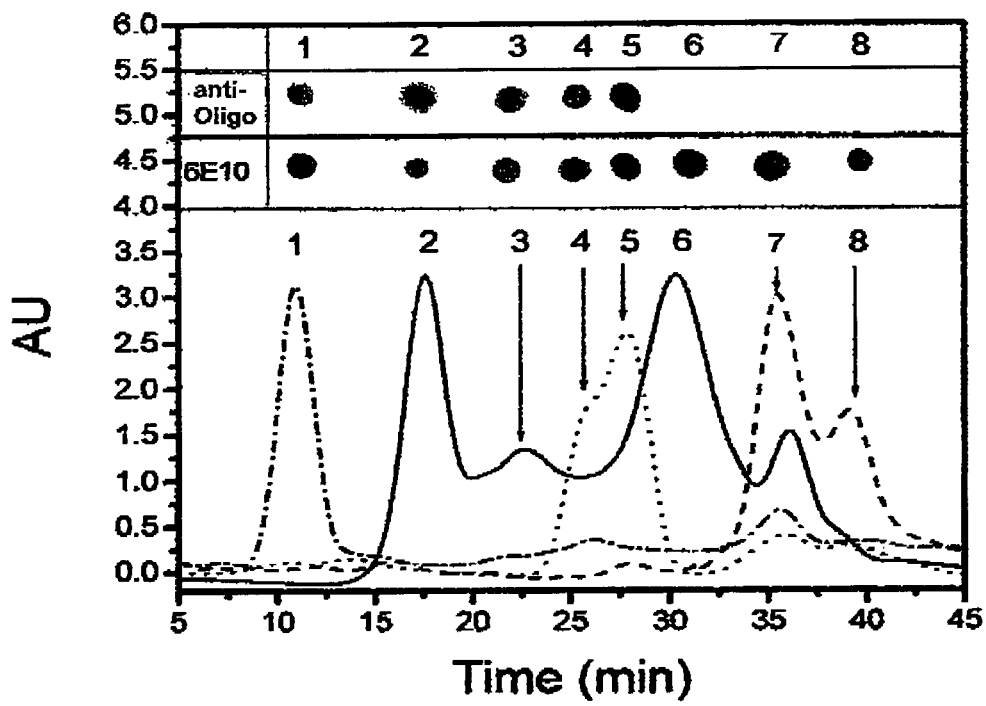
FIG. 5 shows the molecular sizing of Aβ assemblies produced in different solutions over time as determined by dot blot analysis of fractions eluted from a gel filtration column.

A solution of A40 oligomers incubated under different conditions that favour the population of different sizes of oligomers. (———) A40 incubated in DDH$_2$0 (pH 2.54) for 3 days, (— — —) A40 incubated in 50 mM Tris (pH 7.4) 100 mM NaCl for 2 days, (- - - - - - -) 40 Freshly dissolved in 50 mM Tris (pH 7.4), (···) A40 incubated in 50 mM Tris (pH 7.4) for 2 days. The peaks were collected and aliquots from each were dotted on to a nitrocellulose membrane and probed with anti-oligomer or and 6E10 antibodies. The results are shown in FIG. 5.

Peptide aggregates of 40 kDa which elute at a position of approximately 40 kDa, corresponding to an approximate size of an octomer, are recognized by anti-oligomer. Peaks eluting at positions corresponding to tetramer, dimer and monomer do not show reactivity with anti-oligomer.

Example 7

The specificity of anti-oligomer serum produced in Example 2 was analysed by reactivity with other amyloidogenic proteins and peptides by ELISA. This includes analysis of protofibrillar aggregates, low molecular weight oligomers and amyloid fibrils from -synuclein, islet amyloid IAPP, poly glutamine, lysozyme, human insulin and human prion peptide 106-126.

Figure 6:
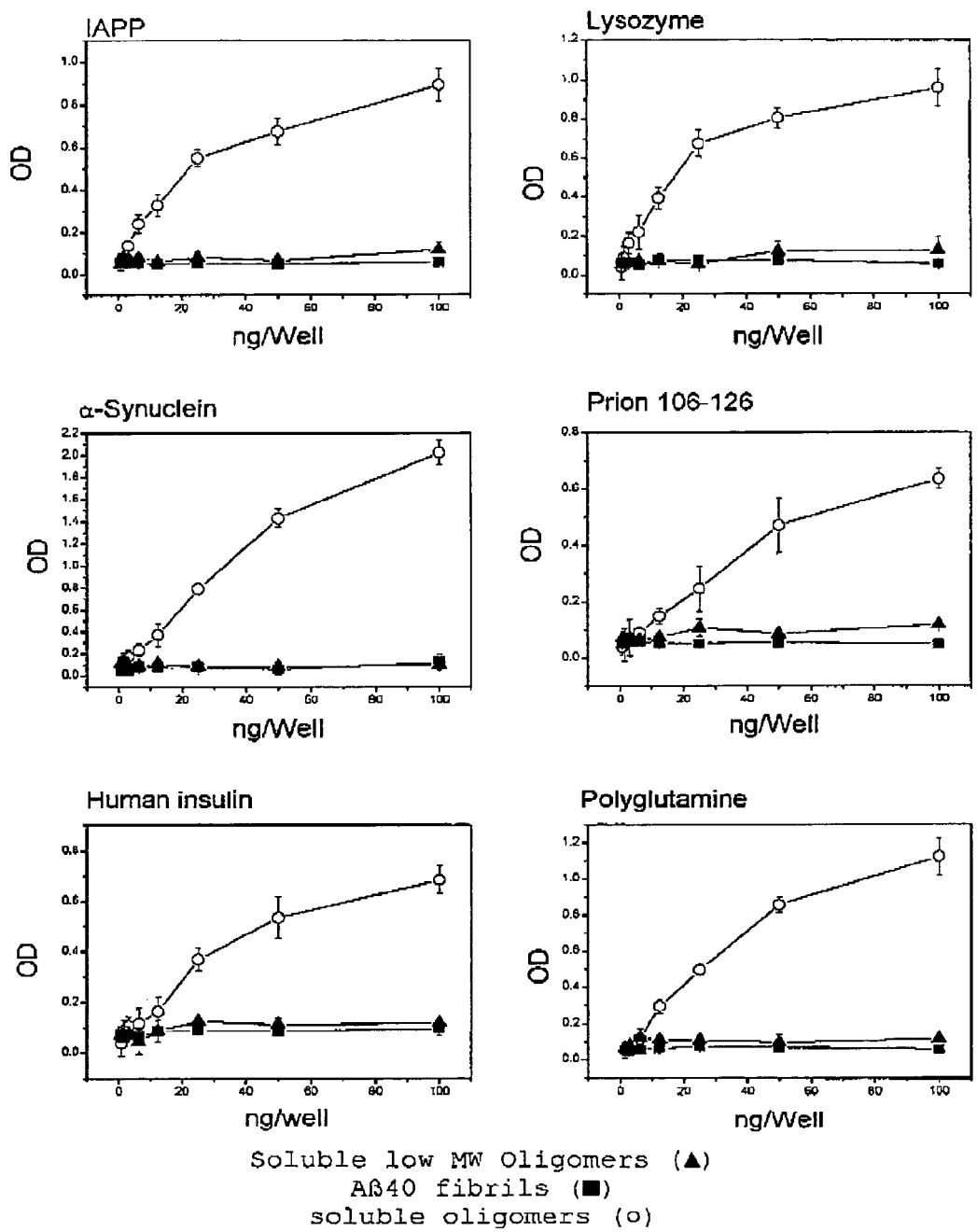
FIG. 6 shows the results of an ELISA assay where various low molecular weight amyloid aggregates, high molecular weight amyloid aggregates and amyloid fibrils are analyzed for anti-oligomer specificity.

Samples were applied to a 96 well plate and analysed by ELISA, which was performed essentially as described in Example 4, using anti-oligomer antiserum (FIG. 6). Soluble low molecular weight oligomers (▲), amyloid peptide aggregates (○) and A40 fibrils (■) were analyzed for each amyloid type. Only the amyloid peptide aggregates are recognized by anti-oligomer, while the soluble low molecular weight oligomers and fibrils give only background values. The type of amyloid is listed at the top of each panel in FIG. 6.

These results indicate that anti-oligomer recognizes a unique common conformational structural feature of the polypeptide backbone in the amyloid peptide aggregates and is not defined by a unique primary amino acid sequence.

Example 8

The ability of anti-oligomer antibody to inhibit neurotoxicity in cell culture was examined.

Inhibition of the cytotoxicity of amyloid peptide aggregates by anti-oligomer antibody is measured using MTT reduction and LDH release toxicity assays in human neuroblastoma SH-SY5Y cells.

For MTT reduction assays, SH-SY5Y human neuroblastoma cells were maintained in DMEM with 10 mM HEPES, 10% fetal bovine serum, 4 mM glutamine, penicillin (200 unit/ml) and streptomycin (200 μg/ml) in 5% $CO_2$ at 37° C. The medium was replaced every 2 days. Cells were differentiated in serum-free DMEM medium with N2 supplement and $1 \times 10^{-5}$ M all-trans retinoic acid before use. Cells were plated at (10,000 cells/well) in 96-well plates and grown overnight. The medium was removed and the amyloid forms to be examined were added in 80 μl of new medium without phenol red. After incubation for 4 h at 37° C., the cells were assayed using an MTT toxicology kit (Tox-1,Sigma) according to the manufacturer's directions.

For LDH release assays, SH-SY5Y cells were prepared and treated with amyloid forms as described above. After 8 h at 37° C., the LDH assay was performed using the LDH toxicology assay kit (Tox-7, Sigma) according to the manufacturer's directions.

Figure 7:
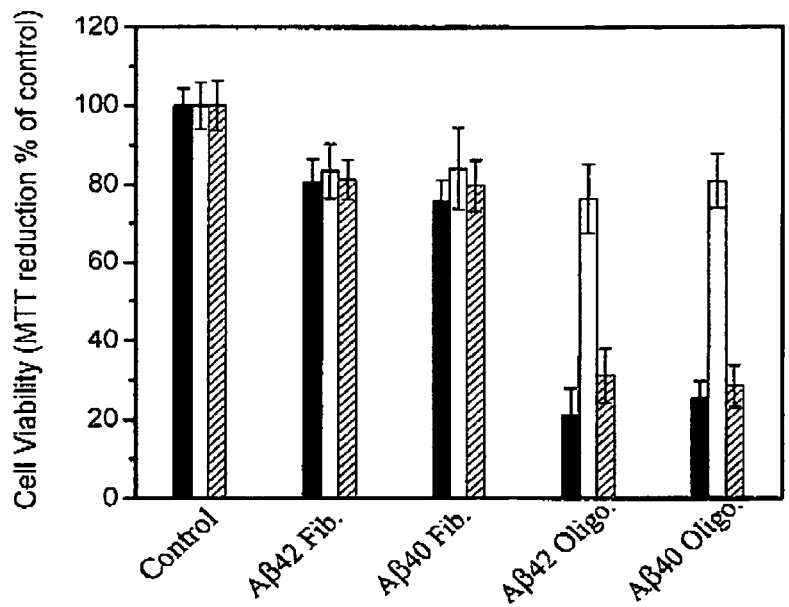
FIG. 7 shows the reduction in cell toxicity of A40 and A42 fibrils (Fib.) and A40 and A42 high molecular weight aggregates (Oligo.) by anti-oligomer antibody using the MTT reduction assay.

FIG. 7 shows the inhibition of A40 and A42 oligomeric intermediate toxicity and A40 and A42 fibril toxicity by anti-oligomer utilizing MTT reduction. Samples were preincubated with (open bars) without (filled bars) an excess of affinity purified anti-oligomer antibody for 30 min or with an equivalent amount of non-immune rabbit IgG (hatched bars) and then assayed for cytotoxicity at a final concentration of 2.5 mM. Anti-oligomer is effective to substantially reduce the toxicity of the oligomeric intermediates (Oligos.). The fibrillar forms are initially substantially non-toxic and are essentially uneffected by anti-oligomer.

Inhibition of the toxicity of other amyloid peptide aggregates including those from -synuclein, islet amyloid polypeptide (IAPP), poly glutamine, lysozyme, human insulin and human prion peptide 106-126 by anti-oligomer utilizing MTT reduction is shown in FIG. 8. FIG. 8 also shows the measurement of cell toxicity and the reducing thereof by anti-oligomer for soluble low molecular weight oligomers and fibrils in a combined average measurement for all of the amyloid types examined (All Sol. and All Fib.).

Figure 9A:
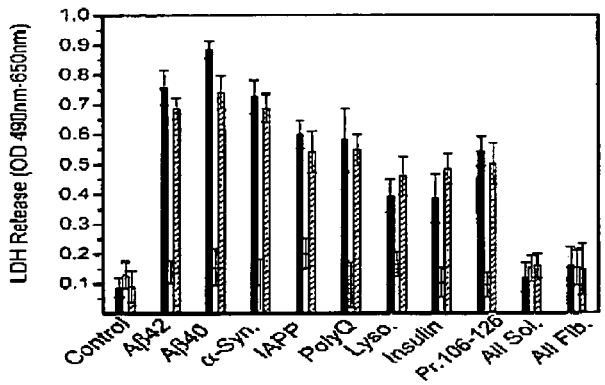
FIGS. 9a and 9b show the reduction in cell toxicity of low molecular weight aggregates (Sol.) high molecular weight aggregates and fibrils (Fib.) of A40, A42, -synuclein, islet amyloid polypeptide (IAPP), poly glutamine, lysozyme, human insulin and human prion peptide 106-126 by anti-oligomer antibody using the LDH release assay.
Figure 9B:
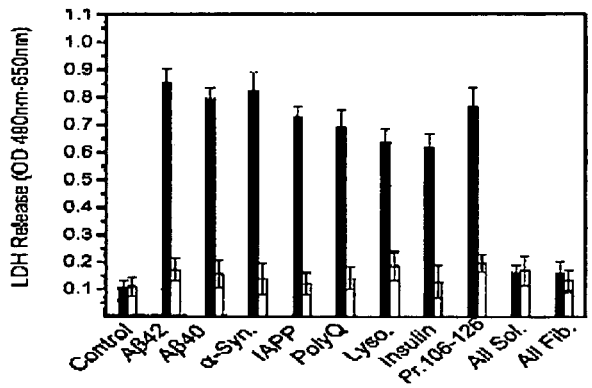

The inhibition of the toxicity of A40, A42, -synuclein, islet amyloid polypeptide (IAPP), poly glutamine, lysozyme, human insulin and human prion peptide 106-126 amyloid peptide aggregates by the anti-oligomer antibody as measured using LDH release assays in human neuroblastoma SH-SY5Y cells is shown in FIGS. 9a and 9b. The soluble oligomer samples were preincubated with (open bars) or without (filled bars) an excess of affinity purified anti-oligomer antibody or with an equivalent amount of non-immune rabbit IgG (hatched bars) for 30 min and then assayed for cytotoxicity at a final concentration of 2.5 mM. FIGS. 9a and 9b also shows the measurement of cell toxicity and the reducing thereof by anti-oligomer for soluble low molecular weight oligomers and fibrils in a combined average measurement for all of the amyloid types examined (All Sol. and All Fib.). FIG. 9b is included for the purpose of clarity and shows the open and filled bars presented in FIG. 9b.

It is clear from the data that inhibition of the toxicity by anti-oligomer antibody occurs with each amyloid peptide aggregate type examined.

The showing that the amyloid peptide aggregates of all of the amyloids examined display significant toxicity and that the toxicity is removed by anti-oligomer indicate that amyloid peptide aggregates share a common structure that may mediate toxicity by a common mechanism. Also indicated is that anti-oligomer is an effective antibody for binding and reducing the toxicity of the general class of amyloid oligomeric intermediates.

Example 9

The specificity of anti-oligomer was examined by dot blot analysis and by ELISA assay.

Figure 10:
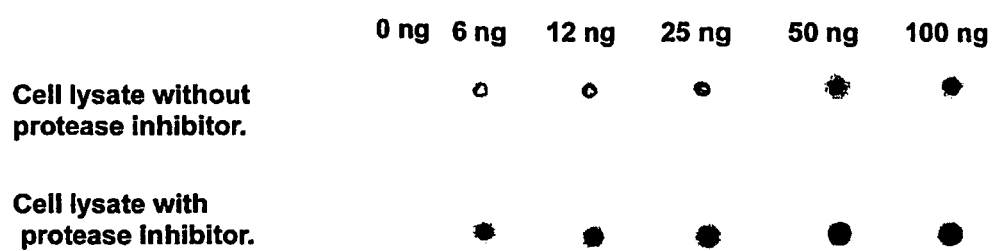
FIG. 10 shows a dot blot analysis which demonstrates the specificity of anti-oligomer antibody in cell extracts.

Dot Blot Analysis:

Soluble SH-SY5Y cell lysate (2.8 ug) was mixed with 0, 6, 12, 25, 50 or 100 ng of A42 amyloid peptide aggregates. The samples were examined by dot blot analysis performed essentially as described in example 4 (FIG. 10).

No immunoreactivity of anti-oligomer is observed with cell lysate in the absence of added amyloid peptide aggregates. Top row: Amyloid peptide aggregates incubated with cell lysate in the absence of protease inhibitor cocktail. Bottom row: Amyloid peptide aggregates incubated with cell lysate in the presence of protease inhibitor cocktail. There is a marked increase in the detectable amyloid peptide aggregates in the presence of protease inhibitors.

Figure 11:
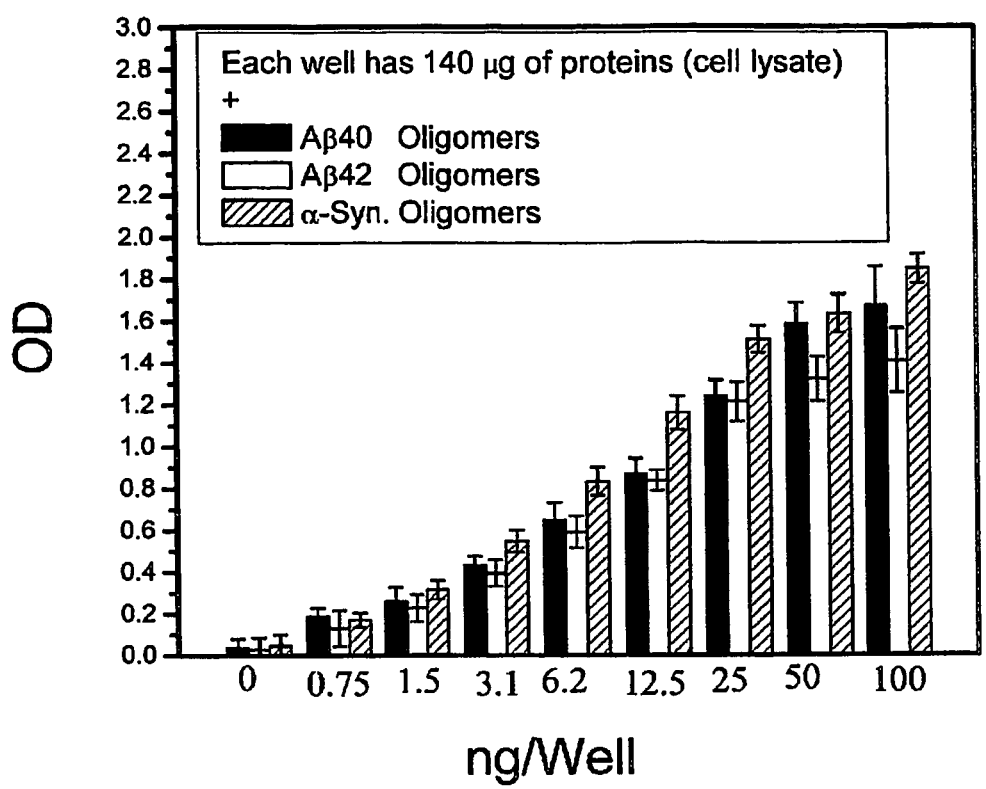
FIG. 11 shows an ELISA assay which demonstrates the specificity of the anti-oligomer antibody in cell extracts.

ELISA Assay:

Soluble SH-SY5Y cell lysate (20 ug) was mixed with increasing amounts of A42, A40 and -synuclein amyloid peptide aggregates and subjected to ELISA assay which was performed essentially as described in Example 4 (FIG. 11). As little as 0.75 ng of amyloid peptide aggregates is detected above the background of the cell lysate in the absence of amyloid peptide aggregates.

As in the dot blot analysis, the detection of the added soluble oligomers when mixed with cell lysate depends on the presence of protease inhibitors. This indicates that soluble amyloid peptide aggregates are sensitive to proteolysis as has been previously reported (Walsh et al. (2002) Nature 416, 535-539).

The unfractionated serum produced in response to repeated immunization with the molecular mimic is remarkably specific for the pathological micellar conformations of the amyloid forming peptides. This suggests that it may provide a means for vaccine development that avoids undesirable inflammatory side effects that have been observed for vaccination using A, since it specifically targets the intermediates without any reactivity against monomeric Aβ or fibrillar deposits (Hardy, D. J. Selkoe (2002) Science 297, 353-356). The finding that soluble oligomers of all amyloids tested are all recognized by this antibody suggests that a vaccine directed against this epitope may be an effective therapeutic approach for a broad spectrum of amyloid diseases.

Example 10

Method of Diagnosis Using an ELISA Assay

Cerebrospinal fluid samples are diluted serially at two-fold dilutions in coating buffer (0.1 M sodium bicarbonate, pH 9.6). 100 μl of the samples are added to wells of 96-well microplates, incubated for 2 hours at 37° C., washed three times with (PBS containing 0.01% Tween 20, PBS-T) and then blocked for 2 h at 37° C. with 3% BSA TBS-T. The BSA used is IgG free (Sigma). The plates are then washed three times with PBS-T and 100 μl of anti-oligomer (1:10,000 dilution in 3% BSA/TBS-T) is added and incubated for 1 hour at 37° C. The plates are washed three times with PBS-T and 100 μl horseradish peroxidase-conjugated anti-rabbit IgG (Promega diluted 1:10,000 in 3% BSA TBS-T) is added and incubated for 1 hour at 37° C. The plates are washed three times with PBS-T and developed using 3,3',5,5'-tetramethylbenzidine (TMB; KPL Gaitherburg, Md.). The reaction is stopped with 100 µL 1 M HCl and the plates read at 450 nm. Binding of the anti-oligomer to the ELISA palte wells indicates the presence of amyloid oligomeric intermediate.

Example 11

Method for Assessing Efficacy of a Treatment Method

The oligomer specific antibody can be utilized in screening for drugs and therapeutic agents that inhibit the formation of amyloid oligomeric intermediates or cause the disassembly or disaggregation of such oligomeric intermediates. In order to screen for drugs that inhibit amyloid oligomer intermediate formation, a test compound or drug is incubated with amyloid peptides under conditions where amyloid oligomeric intermediates would form in the absence of any inhibitory effect. The mixture is assayed by ELISA plates essentially as described in Example 4 determining the amount of amyloid oligomeric intermediates formed. In order to test for compounds, that disassemble or disaggregate oligomeric intermediates, preformed oligomeric intermediates are mixed with a test drug or compound and the mixture is assayed by ELISA determining the amount of oligomeric intermediates present. An inhibitory compound gives rise to a lower amount of amyloid oligomers detected by anti-oligomer antibody in the assay.

Although the foregoing invention has been described in detail for purposes of clarity of understanding, it will be obvious that certain modifications may be practised within the scope of the appended claims. All publications and patent documents cited herein are hereby incorporated by reference in their entirety for all purposes to the same extent as if each were so individually denoted.

What is claimed is:

1. A composition comprising an isolated conformational epitope of a soluble amyloid aggregate which a) forms in a human or animal and b) contributes to amyloid disease;

said conformational epitope comprising five or more monomers, wherein the epitope is affixed to a curved or flat support surface, wherein affixation to the support surface causes the epitope to assume and be constrained in a three-dimensional conformation, wherein the three-dimensional confirmation causes the epitope to be recognized by an antibody that binds an Aβ peptide aggregate that is not a monomer, dimer, trimer, tetramer or Aβ fibril; and wherein the support surface comprises a material selected from; gold, zinc, cadmium, tin, titanium, silver, selenium, gallium, indium, arsenic, silicon, mixtures thereof and combinations thereof.

2. A composition according to claim 1 wherein the epitope composition is conformationally constrained.

3. A composition according to claim 1 wherein the composition is chemically bound to the surface.

4. A composition according to claim 1 wherein the amyloid aggregate has a molecular weight in a range of about 1 kDa to about 100,000,000 kDa.

5. A composition according to claim 1 wherein the epitope comprises an epitope of a toxic species of an amyloid aggregate.

6. A composition according to claim 1 wherein the epitope is chemically bound to the surface.

7. A composition according to claim 6 wherein the epitope comprises a C terminus, wherein the C terminus is bound to the support surface.

8. A composition according to claim 7 wherein the C terminus is bound to the surface by a carboxy thiol linkage.

9. A composition according to claim 8 wherein the surface comprises a gold surface.

10. A composition according to claim 9 wherein the gold surface comprises colloidal gold.

11. A composition according to claim 1 wherein the epitope comprises an epitope of Aβ.

12. A composition according to claim 1 wherein the epitope is coupled to gold on the support surface.

13. A composition according to claim 12 wherein the epitope comprises a C terminus, wherein the C terminus is coupled to gold on the support surface.

14. A composition according to claim 13 wherein the gold comprises colloidal gold.

15. A composition according to claim 1 wherein the surface comprises a surface of a film.

16. A composition according to claim 1 wherein the surface comprises a surface of a sheet.

17. A composition according to claim 1 wherein the surface comprises a surface of a pleated sheet.

18. A composition according to claim 1 wherein the surface comprises a surface of a protein.

19. A composition according to claim 1 wherein the epitope comprises SEQ ID NO. 2.

* * * * *

```
                           SEQUENCE LISTING

<160> NUMBER OF SEQ ID NOS: 10

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
 1               5                   10                  15

Leu Val Phe Phe Ala Glu Asp Val Gly Ser Asn Lys Gly Ala Ile Ile
             20                  25                  30

Gly Leu Met Val Gly Gly Val Val
         35                  40

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
 1               5                   10                  15

Leu Val Phe Phe Ala Glu Asp Val Gly Ser Asn Lys Gly Ala Ile Ile
             20                  25                  30

Gly Leu Met Val Gly Gly Val Val Ile Ala
         35                  40

<210> SEQ ID NO 3
<211> LENGTH: 37
<212> TYPE: PRT
<213> ORGANISM: Homo sapiens

<400> SEQUENCE: 3

Lys Cys Asn Thr Ala Thr Cys Ala Thr Gln Arg Leu Ala Asn Phe Leu
 1               5                   10                  15

Val His Ser Ser Asn Asn Phe Gly Ala Ile Leu Ser Ser Thr Asn Val
             20                  25                  30

Gly Ser Asn Thr Tyr
         35

<210> SEQ ID NO 4
<211> LENGTH: 21
```

```
<212> TYPE: PRT
<213> ORGANISM: Homo sapiens

<400> SEQUENCE: 4

Lys Thr Asn Met Lys His Met Ala Gly Ala Ala Ala Gly Ala Val
 1               5                  10                 15

Val Gly Gly Leu Gly
            20

<210> SEQ ID NO 5
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Lys Gln Gln Gln Gln Gln Gln Gln Gln Gln Gln Gln Gln Gln Gln
 1               5                  10                 15

Gln Gln Gln Gln Gln Gln Gln Gln Gln Gln Gln Gln Gln Gln
            20                  25                 30

Gln Gln Gln Gln Gln Gln Gln Gln Gln Lys Lys
        35                  40

<210> SEQ ID NO 6
<211> LENGTH: 147
<212> TYPE: PRT
<213> ORGANISM: Homo sapiens

<400> SEQUENCE: 6

Met Lys Ala Leu Ile Val Leu Gly Leu Val Leu Ser Val Thr Val
 1               5                  10                 15

Gln Gly Lys Val Phe Glu Arg Cys Glu Leu Ala Arg Thr Leu Lys Arg
            20                  25                 30

Leu Gly Met Asp Gly Tyr Arg Gly Ser Leu Ala Asn Trp Met Cys Leu
        35                  40                  45

Ala Lys Trp Glu Ser Gly Tyr Asn Thr Arg Ala Thr Asn Tyr Asn Ala
     50                  55                  60

Gly Asp Arg Ser Thr Asp Tyr Gly Ile Phe Gln Ile Asn Ser Arg Tyr
 65                  70                  75                  80

Trp Cys Asn Asp Gly Lys Thr Pro Gly Ala Val Asn Ala Cys His Leu
                85                  90                  95

Ser Cys Ser Ala Leu Leu Gln Asp Asn Ile Ala Asp Ala Val Ala Cys
            100                 105                 110

Ala Lys Arg Val Val Arg Asp Pro Gln Gly Ile Arg Ala Trp Val Ala
        115                 120                 125

Trp Arg Asn Arg Cys Gln Asn Arg Asp Val Arg Gln Tyr Val Gln Gly
    130                 135                 140

Cys Gly Val
145

<210> SEQ ID NO 7
<211> LENGTH: 110
<212> TYPE: PRT
<213> ORGANISM: Homo sapiens

<400> SEQUENCE: 7

Met Ala Leu Trp Met Arg Leu Leu Pro Leu Leu Ala Leu Leu Ala Leu
 1               5                  10                 15
```

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 8
<211> LENGTH: 147
<212> TYPE: PRT
<213> ORGANISM: Homo sapiens

<400> SEQUENCE: 8

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
            35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
            115                 120                 125

Ala Leu Leu Ser Pro Tyr Ser Tyr Ser Thr Thr Ala Val Val Thr Asn
            130                 135                 140

Pro Lys Glu
145

<210> SEQ ID NO 9
<211> LENGTH: 140
<212> TYPE: PRT
<213> ORGANISM: Homo sapiens

<400> SEQUENCE: 9

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

```
Thr Val Glu Gly Ala Gly Ser Ile Ala Ala Ala Thr Gly Phe Val Lys
                85              90                  95

Lys Asp Gln Leu Gly Lys Asn Glu Glu Gly Ala Pro Gln Glu Gly Ile
            100             105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130             135             140

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
 1               5
```